(12) United States Patent
Masuda et al.

(10) Patent No.: US 6,322,516 B1
(45) Date of Patent: Nov. 27, 2001

(54) BLOOD-PRESSURE MONITOR APPARATUS

(75) Inventors: Hiroshi Masuda, Komaki; Akihiro Yokozeki, Nagoya; Hidekatsu Inukai; Yoshihisa Miwa, both of Komaki, all of (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/696,981

(22) Filed: Oct. 27, 2000

(51) Int. Cl.[7] .................................................. A61B 5/00
(52) U.S. Cl. .................... 600/493; 600/494; 600/490; 600/496
(58) Field of Search ................. 600/485, 493–6, 600/500

(56) References Cited

U.S. PATENT DOCUMENTS

| 4,873,987 | * | 10/1989 | Djordjevich et al. ............... 600/494 |
| 5,533,511 | * | 7/1996 | Kaspari et al. ...................... 600/485 |
| 5,752,920 |   | 5/1998 | Ogura et al. . |
| 6,196,974 | * | 3/2001 | Miwa .................................. 600/494 |

FOREIGN PATENT DOCUMENTS 10-43147   2/1998   (JP) .

* cited by examiner

Primary Examiner—Robert L. Nasser
(74) Attorney, Agent, or Firm—Oliff & Berridge, PLC

(57) ABSTRACT

A blood-pressure monitor, including a blood-pressure measuring device including a cuff, an information obtaining device which iteratively obtains, from a living subject, physical information which changes with change of blood pressure of the subject, a measurement starting device for starting a measurement of the blood-pressure measuring device, when a subsequent piece of information obtained by the obtaining device after the measuring device has measured a last blood pressure of the subject in a last measurement thereof has been deviated by not less than a predetermined amount from an initial piece of information obtained by the obtaining device when the measuring device measured the last blood pressure of the subject, a display device which displays a graph representing the pieces of information obtained by the obtaining device, and a control device which controls the display device to display the graph representing the initial piece of information and each one of subsequent pieces of information iteratively obtained by the obtaining device after the measuring device has measured the last blood pressure of the subject, so that the initial piece of information and the each one subsequent piece of information can be compared with each other.

10 Claims, 12 Drawing Sheets

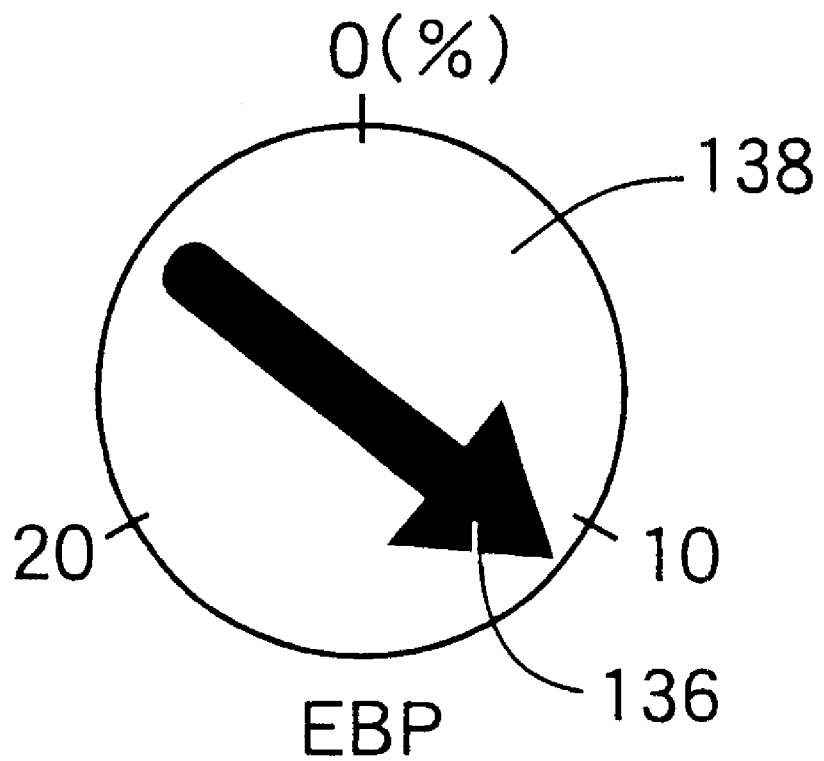

BLOOD-PRESSURE MONITOR APPARATUS

BACKGROUND OF INVENTION

1. Field of Invention

The present invention relates to a blood-pressure monitor apparatus which monitors the chance of blood pressure of a living subject, based on blood-pressure-relating information which changes in relation with the change of blood pressure of the subject.

2. Related Art Statement

As a pulse-wave-propagation-velocity ("PWPV") relating information which relates to a velocity at which a pulse wave propagates through an artery of a living subject, there is known a propagation time, DT, in which the pulse wave propagates between two different portions of the artery, or the propagation velocity, $V_M$, (m/s) itself. It is known that the PWPV-relating information has, within a certain range, a substantially proportional relationship with the blood pressure, BP, (mmHg) of the living subject. Hence, there has been proposed a blood-pressure ("BP") monitor apparatus which determines, in advance, unknown coefficients, $\alpha$ and $\beta$, of a linear expression, $EBP=\alpha(DT)+\beta$ ($\alpha$ is a negative constant), or $EBP=\alpha(V_C)+\beta$ ($\alpha$ is a positive constant), based on subject's BP value, BP, and a piece of PWPV-relating information (DT or $V_M$) both of which are measured in advance, and then determines, according to the thus determined linear expression, an estimated BP value, EBP, of the subject based on each one of pieces of PWPV-relating information iteratively obtained after the last BP measurement using a cuff. Thus, the BP monitor apparatus can monitor the blood pressure of the subject. If one of the estimated BP values EBP iteratively determined after the last BP measurement has largely deviated from the estimated BP value at the time of the last BP measurement, the BP monitor apparatus starts a BP measurement using the cuff.

Meanwhile, it is known that the blood pressure of a living subject is regulated by the cardiac output (1/min), and the peripheral vascular resistance, of the subject. More specifically described, as the cardiac output increases, the blood pressure increases; and as the cardiac output decreases, the blood pressure decreases. As the peripheral vascular resistance increases, that is, the peripheral blood vessels contract, the blood pressure increases; and as the peripheral vascular resistance decreases, that is, the peripheral blood vessels expand, the blood pressure decreases. The cardiac output is obtained as the product of stroke volume (i.e., volume of blood Output from the heart per stroke or beat) and heart rate. Therefore, heart-rate-relating information which relates to heart rate, such as heart (pulse) rate itself, or pulse period, changes with the change of the blood pressure. In addition, as the peripheral vascular resistance increases, i.e., the peripheral blood vessels contract, the area enveloped by the waveform of each of heartbeat-synchronous pulses of a peripheral pulse wave detected from subject's peripheral portion, decreases. Thus, the area of each pulse of the peripheral pulse wave is influenced by the change of the peripheral vascular resistance. That is, the area of each pulse of the peripheral pulse wave changes with the change of the blood pressure. These phenomena are utilized by another BP monitor apparatus which starts a BP measurement using a cuff if one of pieces of pulse-rate-relating information iteratively obtained, or one of pulse areas iteratively obtained, after the last BP measurement using the cuff has deviated by not less than a predetermined amount from the piece of pulse-rate-relating information, or the pulse area, at the time of the last BP measurement. An example of this BP monitor apparatus is disclosed in Japanese Patent Publication No. 10-43147 and the corresponding U.S. Pat. No. 5,752,920.

However, the conventional BP monitor apparatuses do not display any piece of BP-relating information, or display only the current one of pieces of BP-relating information iteratively obtained after the last BP measurement using the cuff. Therefore, a person such as the subject as a patient or a medical staff who attends the patient cannot judge, from the screen image displayed by each conventional monitor apparatus, that the patient's current condition is not at a critical level which needs a BP measurement using the cuff, but is near to that level, or that the patient's current condition has not changed so much from his or her condition at the time of the last BP measurement. In addition, regarding the conventional BP monitor apparatus which displays only the current one of pieces of BP-relating information iteratively obtained after the last BP measurement, it may be difficult for a person to select an appropriate threshold value, relative to the piece of BP-relating information at the time of the last BP measurement, that is used in judging whether the current piece of BP-relating information is abnormal, that is, whether a BP measurement using the cuff is needed.

In addition, the relationship between subject's blood pressure and PWPV-relating information changes because it is influenced by the condition of subject's central body portion, such as the condition of cardiac muscle, and the condition of subject's peripheral body portion, such as the hardness of peripheral blood vessels or the resistance to blood flows. Therefore, in the BP monitor apparatus disclosed in the above-indicated Japanese Patent Publication No. 10-43147 (and the U.S. Pat. No. 5,752,920), the heart-rate-relating information is used as the central-side information, the area of each pulse of the peripheral pulse wave is used as the peripheral-side information and, if the current PWPV-relating information (or the current estimated BP value determined based on the current PWPV-relating information) has changed by not less than a predetermined amount from the PWPV-relating information (or the estimated BP value) at the time of the last BP measurement and simultaneously if the heart-rate-relating information and/or the area of each pulse of the peripheral pulse wave has changed by not less than a predetermined amount from the heart-rate-relating information and/or the area of one pulse of the peripheral pulse wave at the time of the last BP measurement, a BP measurement using the cuff is started.

However, in the above conventional BP monitor apparatus which uses plural sorts of BP-relating information in judging whether a BP measurement should be started, no pieces of BP-relating information of each sort are displayed, or only the current one of pieces of BP-relating information of each sort, iteratively obtained after the last BP measurement, or a time-wise change of the pieces of BP-relating information of each sort is displayed. Therefore, it is more difficult for a person to judge, from the screen image displayed by the BP monitor apparatus, that the patient's current condition is not at a critical level which needs a BP measurement using the cuff, but is near to that level, or that the patient's current condition has not changed so much from his or her condition at the time of the last BP measurement, than to judge, based on a single sort of BP-relating information, whether a BP measurement should be started. In addition, even when the BP monitor apparatus may start a BP measurement using the cuff, the display device of the apparatus informs only that the abnormality of BP-relating information has occurred, and does not inform which sort of BP-relating information has become abnormal.

For example, in the case of the BP monitor apparatus which starts a BP measurement using the cuff if the current PWPV-relating information has changed by not less than a predetermined amount from the PWPV-relating information at the time of the last BP measurement and simultaneously if the heart-rate-relating information and/or the area of each pulse of the peripheral pulse wave has changed by not less than a predetermined amount from the heart-rate-relating information and/or the area of one pulse of the peripheral pulse wave at the time of the last BP measurement, a person cannot judge whether the PWPV-relating information and the heart-rate-relating information have largely changed, whether the PWPV-relating information and the area of each pulse of the peripheral pulse wave have largely changed, or whether all of the PWPV-relating information, the heart-rate-relating information, and the area of each pulse of the peripheral pulse wave have largely changed.

Moreover, in the above conventional BP monitor apparatus, since plural sorts of BP-relating information are employed in judging whether a BP measurement should be started, a person has a high degree of freedom in selecting respective threshold values which are used in judging whether a BP measurement should be started. Thus, it is more difficult for a person to select, for each of the plural sorts of BP-relating information, an appropriate threshold value, relative to the piece of BP-relating information of the each sort at the time of the last BP measurement, that is used in judging whether a BP measurement using the cuff should be started, than to select, for a single sort of BP-relating information, an appropriate threshold value to be used in judging whether a BP measurement should be started.

SUMMARY OF INVENTION

It is therefore an object of the present invention to provide a blood-pressure monitor apparatus which monitors the change of blood pressure of a living subject, based on the blood-pressure-relating information which changes in relation with the change of blood pressure of the subject, and which enables a person to recognize to what degree the current piece of blood-pressure-relating information has deviated from the piece of blood-pressure-relating information at the time of the last blood pressure measurement.

The above object may be achieved according to a first feature of the present invention, which provides a blood-pressure monitor apparatus, comprising a blood-pressure measuring device which includes an inflatable cuff adapted to apply a pressing pressure to a portion of a living subject and which measures a blood pressure of the subject by changing the pressure of the cuff applied to the portion of the subject; a blood-pressure-elating-information obtaining device which iteratively obtains, from the living subject, blood-pressure-relating information which changes with change of the blood pressure of the subject; a blood-pressure-measurement starting means for starting a blood-pressure measurement of the blood-pressure measuring device, when a subsequent piece of blood-pressure-relating information obtained by the blood-pressure-relating-information obtaining device after the blood-pressure measuring device has measured a last blood pressure of the living subject in a last blood pressure measurement thereof has deviated by not less than a predetermined amount from an initial piece of blood-pressure-relating information obtained by the obtaining device when the blood-pressure measuring device measured the last blood pressure of the subject; a display device which displays a graph representing the pieces of blood-pressure-relating information obtained by the blood-pressure-relating-information obtaining device; and a control device which controls the display device to display the graph representing the initial piece of blood-pressure-relating information and each one of subsequent pieces of blood-pressure-relating information iteratively obtained by the obtaining device after the blood-pressure measuring device has measured the last blood pressure of the subject, so that the initial piece of blood-pressure-relating information and the each one subsequent piece of blood-pressure-relating information can be compared with each other on the display device.

The present BP monitor apparatus displays, on the display device, the graph representing the initial piece of blood-pressure-relating information at the time when the blood-pressure measuring device measured the last blood pressure of the subject, and each one of subsequent pieces of blood-pressure-relating information iteratively obtained by the obtaining device after the blood-pressure measuring device has measured the last blood pressure of the subject, so that the initial piece of blood-pressure-relating information and the each one subsequent piece of blood-pressure-relating information can be compared with each other on the display device. Thus, a person such as the living subject (e.g. a patient) or a medical staff can recognize, from the graph, to what degree each subsequent piece of blood-pressure-relating information has deviated from the initial piece of blood-pressure-relating information at the time of the last blood pressure measurement.

The above object may be achieved according to a second feature of the present invention, which provides a blood-pressure monitor apparatus, comprising a blood-pressure measuring device which includes an inflatable cuff adapted to apply a pressing pressure to a portion of a living subject and which measures a blood pressure of the subject by changing the pressure of the cuff applied to the portion of the subject; a blood-pressure-relating-information obtaining device which iteratively obtains, from the living subject, blood-pressure-relating information which changes with change of the blood pressure of the subject; a blood-pressure-measurement starting means for starting a blood-pressure measurement of the blood-pressure measuring device, when a subsequent piece of blood-pressure-relating information obtained by the blood-pressure-relating-information obtaining device after the blood-pressure measuring device has measured a last blood pressure of the living subject in a last blood pressure measurement thereof has deviated by not less than a predetermined amount from an initial piece of blood-pressure-relating information obtained by the obtaining device when the blood-pressure measuring device measured the last blood pressure of the subject; a display device which displays a graph representing the pieces of blood-pressure-relating information obtained by the blood-pressure-relating-information obtaining device; and a control device which controls the display device to display the graph representing the initial piece of blood-pressure-relating information and a most deviated one of subsequent pieces of blood-pressure-relating information iteratively obtained by the obtaining device after the blood-pressure measuring device has measured the last blood pressure of the subject, so that the initial piece of blood-pressure-relating information and the most deviated subsequent piece of blood-pressure-relating information can be compared with each other on the display device, the most deviated subsequent piece of blood-pressure-relating information being most deviated from the initial piece of blood-pressure-relating information, than any other subsequent piece of blood-pressure-relating information.

The present BP monitor apparatus displays, on the display device, the graph representing the initial piece of bloodpressure-relating information at the time when the blood-pressure measuring device measured the last blood pressure of the subject, and the most deviated one of the subsequent pieces of blood-pressure-relating information iteratively obtained by the obtaining device after the blood-pressure measuring device has measured the last blood pressure of the subject, so that the initial piece of blood-pressure-relating information and the most deviated subsequent piece of blood-pressure-relating information can be compared with each other on the display device. Thus, a person can recognize, from the graph, to what degree the most deviated subsequent piece of blood-pressure-relating information has deviated from the initial piece of blood-pressure-relating information at the time of the last blood pressure measurement.

BRIEF DESCRIPTION OF DRAWINGS

The above and optional objects, features, and advantages of the present invention will be better understood by reading the following detailed description of the preferred embodiments of the invention, when considered in conjunction with the accompanying drawings, in which:

FIG. 11 is a view showing a proportion of an amount of change of an estimated BP value EBP that is displayed, in place of the radar chart 98 (FIG. 5), in a BP-relating-information display area 96 of a display screen 94 of a display device 32 which is employed in another BP monitor apparatus as a fifth embodiment of the present invention;

DESCRIPTION OF PREFERRED EMBODIMENTS

Hereinafter, there will be described a blood-pressure ("BP") monitor apparatus 8 embodying the present invention, by reference to FIGS. 1 to 7.

Figure 1:
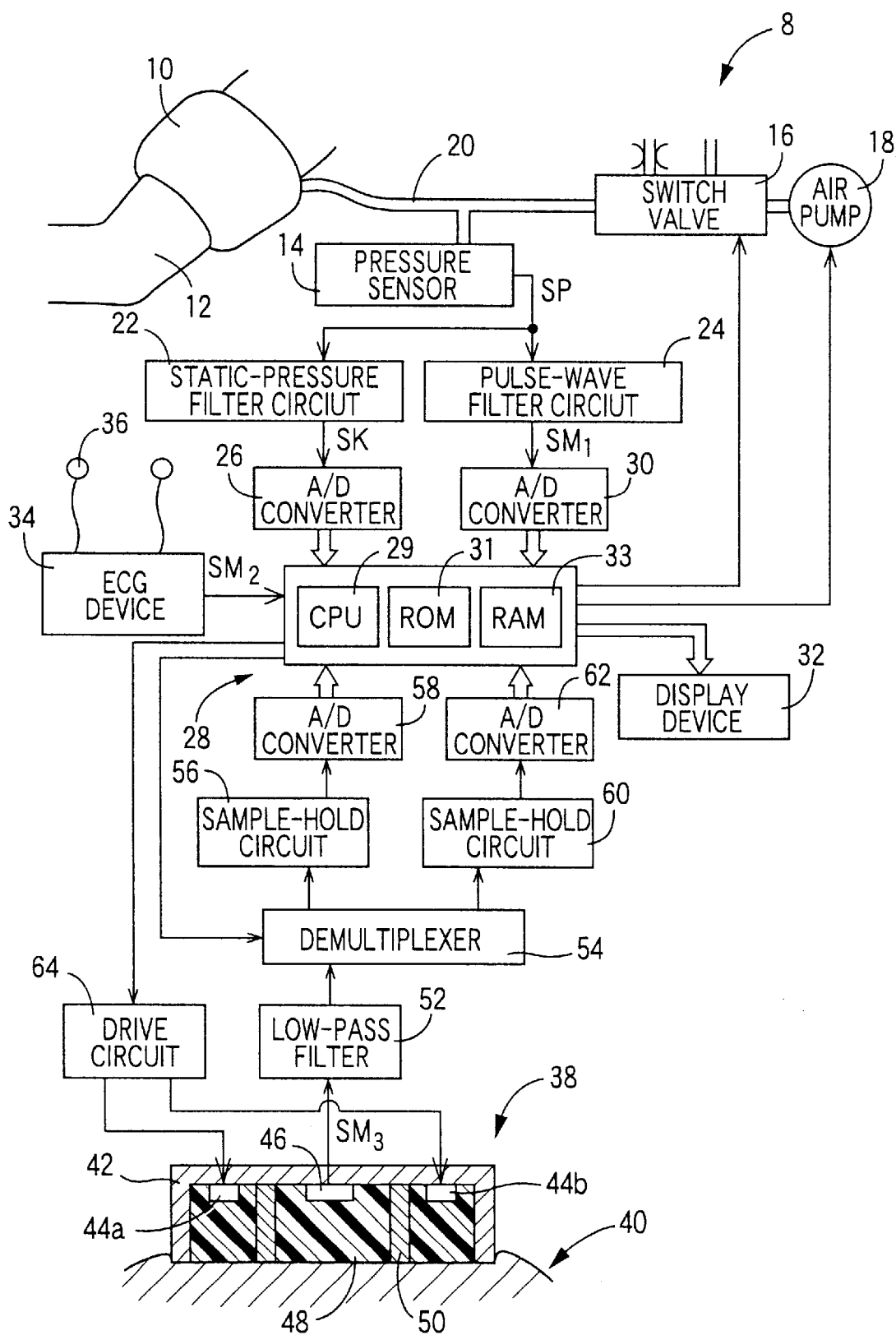
FIG. 1 is a diagrammatic view of a circuit arrangement of a blood-pressure (BP) monitor apparatus embodying the present invention.

In FIG. 1, the BP monitor apparatus 8 includes a cuff 10 which includes a rubber bag and a belt-like cloth bag in which the rubber bag is accommodated. The cuff 10 is wound around, e.g., an upper arm 12 of a patient as a living subject. The monitor apparatus 8 additionally includes a pressure sensor 14, a switch valve 16, and an air pump 18 which are connected to the cuff 10 via piping 20. The switch valve 16 is selectively placed in three states, that is, a pressure-supply state in which the valve 16 allows pressurized air to be supplied from the air pump 18 to the cuff 10, a slow-deflation state in which the valve 16 allows the pressurized air to be slowly deflated from the cuff 10, and a quick-deflation state in which the valve 16 allows the pressurized air to be quickly deflated from the cuff 10.

The pressure sensor 14 detects an air pressure in the cuff 10, and supplies a pressure signal, SP, representing the detected pressure, to a static-pressure filter circuit 22 and a pulse-wave filter circuit 24. The static-pressure filter circuit 22 includes a low-pass filter which selects, from the pressure signal SP, a cuff-pressure signal, SK, representing a static pressure contained in the pressure represented by the pressure signal SP. The cuff-pressure signal SK is supplied to an electronic control device 28 via an analog-to-digital converter ("A/D") converter 26. The pulse-wave filter circuit 24 includes a band-pass filter which selects, from the pressure signal SP, a pulse-wave signal, $SM_1$, representing oscillatory components contained in the pressure represented by the pressure signal SP, that is, a cuff pulse wave produced in the cuff 10. The pulse-wave signal $SM_1$, is supplied to the control device 28 via an A/D converter 30. The cuff pulse wave represented by the pulse-wave signal SM1 is an oscillatory pressure wave that is produced from a brachial artery (not shown) of the patient in synchronism with the heartbeat of the patient and is transmitted to the cuff 10 worn on the upper arm 12 of the patient.

The control device 28 is provided by a microcomputer including a central processing unit ("CPU") 29, a read only memory ("ROM") 31, a random access memory ("RAM") 33, and an I/O port (not shown). The CPU 29 processes, according to control programs pre-stored in the ROM 31, input signals while utilizing a temporary-storage function of the RAM 33, and outputs, via the I/O port, drive signals to the switch valve 16 and the air pump 18 to control the same 16, 18.

An electrocardiograph ("ECG") device 34 includes a plurality of electrodes 36 which are put on predetermined locations on the patient, and continuously detects, through the electrodes 36, an electrocardiogram ("ECG") waveform representing action potential of the cardiac muscle of the patient. The ECG device 34 supplies an ECG signal, $SM_2$, representing the ECG waveform, to the control device 28. The ECG waveform represented by the ECG signal $SM_2$ includes a Q-wave or an R-wave representing a time when the heart of the patient starts outputting blood toward the aorta. Thus, the ECG device 34 functions as a central or first pulse-wave detecting device.

A photoelectric-pulse-wave detecting probe 38 is for use in blood-oxygen-saturation measurements. The probe 38 detects, in the form of a photoelectric pulse wave, a pulse wave transmitted to a peripheral artery including capillaries. Thus, the probe 38 functions as a peripheral or second pulse-wave detecting device. For example, the probe 38 is held in close contact with a body surface (i.e., skin) 40 of a portion (e.g., finger) of the patient, with the help of a fastening band (not shown). The probe 38 includes a housing 42, a plurality of first light-emitting elements 44a, a plurality of second light-emitting elements 44b, a light-receiving element 46, a transparent resin 48, and an annular light-shield member 50. The housing 42 has a container-like cylindrical shape with a circular bottom wall and a circular opening. The first and second light-emitting elements 44a, 44b are supported by a radially outer portion of the circular bottom wall of the housing 42, such that the first and second elements 44a, 44b are alternate with each other in the circumferential direction of the circular bottom wall. The elements 44a, 44b are provided by, e.g., light-emitting diodes ("LEDs"). Hereinafter, the first and second light-emitting elements 44a, 44b will be referred to as the light-emitting elements 44, in the case where it is not necessary to distinguish the first and second elements 44a, 44b from each other. The light-receiving element 46 is supported by a central portion of the circular bottom wall of the housing 42, and is provided by, e.g., a photodiode or a phototransistor. The transparent resin 48 completely fills an inner space of the housing 42 to cover the light-emitting elements 44 and the light-receiving element 46. The annular light-shield member 50 is provided, in the housing 42, between the light-emitting elements 44 and the light-receiving element 46, and prevents the light emitted from the light-emitting elements 44 and reflected from the body surface 40, from being incident to the light-receiving element 46. Thus, the light-shield member 50 assures that the light emitted from the light-emitting elements 44 and reflected from the tissue (e.g., capillaries) under the body surface 40 are incident to the light-receiving element 46.

The first light-emitting elements 44a emit a red light having, e.g., a 660 nm wavelength, and the second light-emitting elements 44b emit an infrared light having, e.g., an 800 nm wavelength. The first and second light-emitting elements 44a, 44b alternately emit the red light and the infrared light, each for a predetermined time duration, at a predetermined frequency. The respective lights emitted from the light-emitting elements 44 and reflected from the capillaries of the tissue under the body surface 40 are received by the common light-receiving element 46. The first and second light-emitting elements 44a, 44b may emit respective lights whose wavelengths are different from the above-indicated wavelengths, so long as oxygenated hemoglobin and reduced hemoglobin exhibit largely different absorption constants with respect to the red light emitted by the first elements 44a, and exhibit a substantially same absorption constant with respect to the infrared light emitted by the second elements 44b, i.e., both reflect the infrared light.

The light-receiving element 46 outputs, to a low-pass filter 52, a photoelectric-pulse-wave signal, $SM_3$, representing the amount of light received thereby. An amplifier may be provided, as needed, between the element 46 and the low-pass filter 52. The low-pass filter 52 removes, from the photoelectric-pulse-wave signal $SM_3$, noise having higher frequencies than that of the pulse wave, and supplies the filtered signal $SM_3$ to a demultiplexer 54. The photoelectric pulse wave represented by the photoelectric-pulse-wave signal $SM_3$ is a volumetric pulse wave that is produced in synchronism with the heartbeat of the patient.

The demultiplexer 54 is switched, in response to switch signals supplied from the control device 28, in synchronism with the alternate light emissions of the first and second light-emitting elements 44a, 44b, so that the demultiplexer 54 supplies an electric signal, $SM_R$, representing the red light, to the I/O port of the control device 28 via a sample-hold circuit 56 and an A/D converter 58, and supplies an electric signal, $SM_{IR}$, representing the infrared light, to the I/O port of the control device 28 via a sample-hold circuit 60 and an A/D converter 62. The sample-hold circuits 56, 60 hold or keep the electric signals $SM_R$, $SM_{IR}$ input thereto, until the A/D converters 58, 62 finish the conversions of the prior electric signals $SM_R$, $SM_{IR}$.

The CPU 29 of the control device 28 carries out, according to the control programs pre-stored in the ROM 31, a measuring operation while utilizing the temporary-storage function of the RAM 33. More specifically described, the control device 28 outputs a control signal to a drive circuit 64 to cause the first and second light-emitting elements 44a, 44b to alternately emit the red and infrared lights at the predetermined frequency, each for the predetermined time duration, and outputs a switch signal to the demultiplexer 54 in synchronism with the alternate light emissions of the first and second elements 44a, 44b. Thus, the electric signal $SM_R$ is supplied to the sample-hold circuit 56, and the electric signal $SM_{IR}$ is supplied to the sample-hold circuit 60. The CPU 29 calculates a blood oxygen saturation of the patient based on respective magnitudes of the electric signals $SM_R$, $SM_{IR}$ according to a mathematical expression which is pre-stored in the ROM 31. Since this process is well known in the art, no description is provided here.

The BP monitor apparatus 8 additionally includes a display device 32 which is provided by a cathode ray tube ("CRT") or a liquid crystal display ("LCD") and which is connected to the I/O port of the control device 28.

Figure 2:
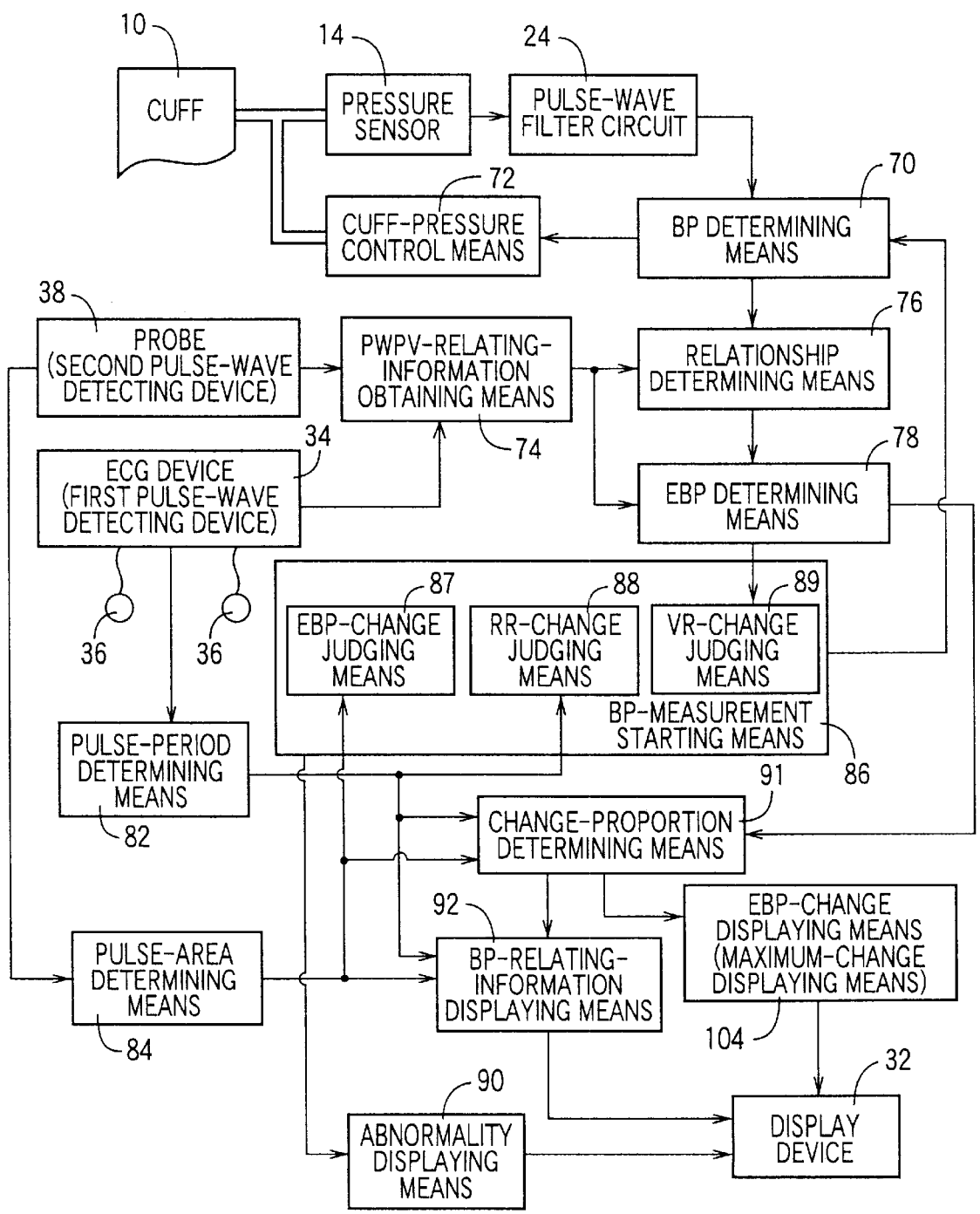
FIG. 2 is a diagrammatic view for explaining important control functions of an electronic control device 28 of the BP monitor apparatus.

FIG. 2 shows various control functions of the electronic control device 28 of the BP monitor apparatus 8. In FIG. 2, a cuff-pressure control means 72 quickly increases the pressing pressure of the cuff 10 wound around the upper arm 12 of the patient, up to a predetermined target pressure value, PCM, (e.g., 180 mmHg) and then slowly decreases the pressure of the cuff 10 at a low rate of 3 mmHg/sec. During the slow cuff deflation period, a BP determining means 70 continuously obtains the pulse-wave signal $SM_1$, and determines a systolic BP value, $BP_{SYS}$, a mean BP value, $BP_{MEAN}$, and a diastolic BP value, $BP_{DIA}$, based on the change of respective amplitudes of heartbeat-synchronous pulses of the signal SM1, according to a well-known oscillometric BP determining method.

Figure 3:
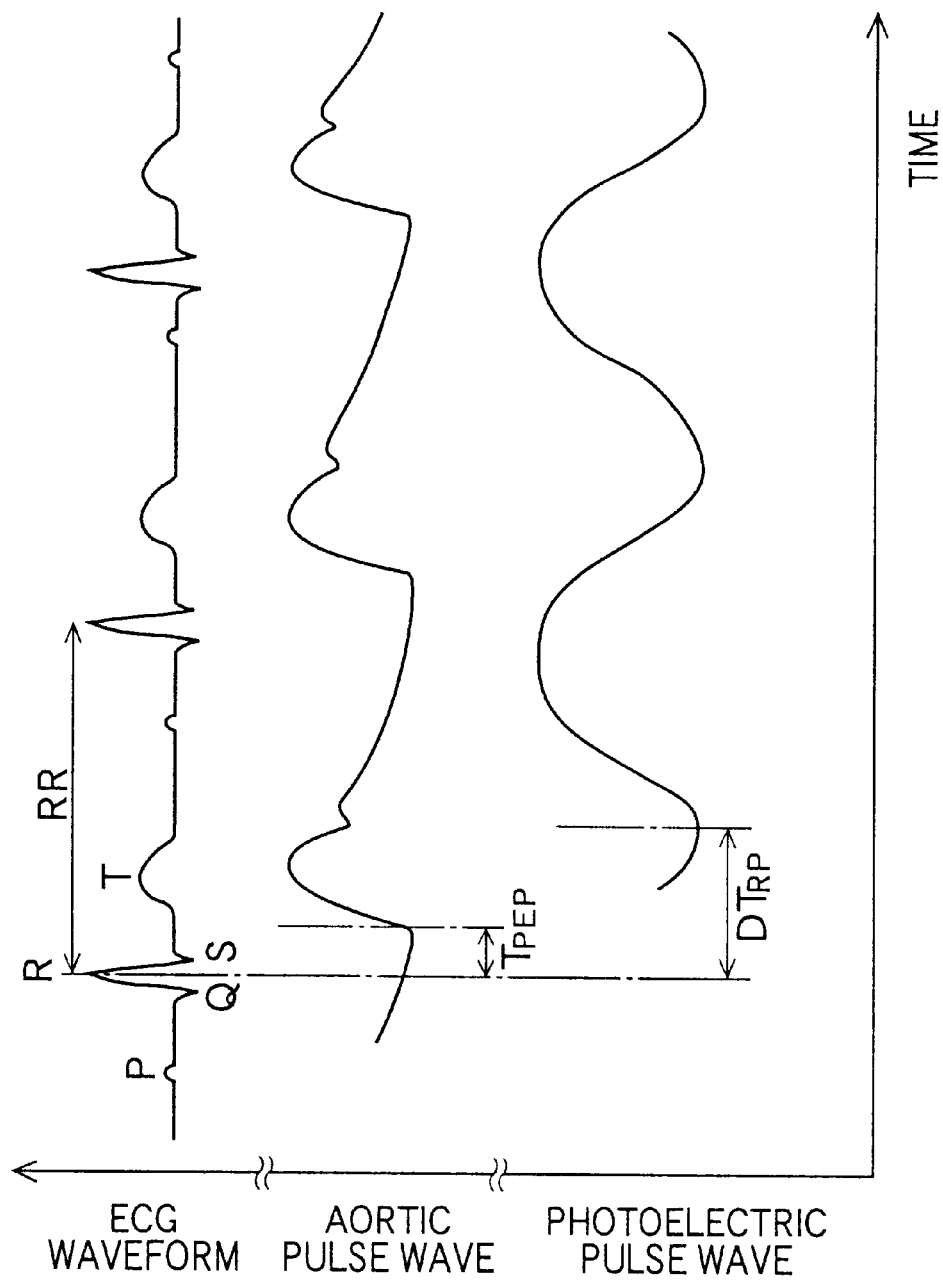
FIG. 3 is a view for explaining a manner in which the control device 28 determines a time difference, $DT_{RP}$.

A pulse-wave-propagation-velocity ("PWPV") relating information obtaining means 74 as a sort of BP-relating-information obtaining means includes a time-difference calculating means for successively calculating, as illustrated in FIG. 3, a time difference (i.e., pulse-wave propagation time), $DT_{RP}$, between a predetermined periodic point (e.g., R-wave) on each of successive heartbeat-synchronous pulses of the ECG waveform detected by the ECG device 34, and a predetermined periodic point (e.g., rising point or lower-peak point) on a corresponding one of successive heartbeat-synchronous pulses of the photoelectric pulse wave detected by the probe 38. The PWPV-relating-information obtaining means 74 successively calculates, based on the time difference $DT_{RP}$ successively calculated by the time-difference calculating means, a pulse-wave propagation velocity, $V_m$, (m/sec) at which the pulse wave propagates through the artery of the patient, according to the following expression (1) that is pre-stored in the ROM 31:

$$V_M = L/(DT_{RP} - T_{PEP}) \quad (1)$$

In the above expression (1), L (m) is the distance from the left ventricle of the heart of the patient, via the aorta, to the location where the probe 38 is worn on the patient; and $T_{PEP}$ (sec) is the pre-ejection period from the R-wave of the ECG waveform to the lower-peak point of the aortic pulse wave. L and $T_{PEP}$ are constants which are experimentally obtained in advance. However, the PWPV-relating-information obtaining means 74 may be modified to calculate a pulse-wave propagation velocity $V_M$ for every second, third, . . . , heartbeat-synchronous pulse of each of the ECG waveform detected by the ECG device 34 and the photoelectric pulse wave detected by the probe 38.

A relationship determining means 76 determines coefficients, α and β, of the following expression (2) or (3) as a relationship between BP and PWPV-relating information, based on a systolic BP value $BP_{SYS}$ determined by the BP determining means 70 and a pulse-wave propagation time $DT_{RP}$, or a pulse-wave propagation velocity $V_M$, measured during the current BP measurement in which the systolic BP value $BP_{SYS}$ is determined (e.g., an average of a plurality of pulse-wave propagation times $DT_{RP}$, or an average of a plurality of pulse-wave propagation velocities $V_M$, measured during the current BP measurement):

$$EBP = \alpha(DT_{RP}) = \beta \quad (2)$$

where α is a negative constant and β is a positive constant.

$$EBP = \alpha(V_M) + \beta \quad (3)$$

where α is a positive constant and β is a positive constant.

However, the coefficients α, β of the expression (2) or (3) may be determined based on a mean BP value $BP_{MEAN}$, or a diastolic BP value $BP_{DIA}$, determined by the BP determining means 70. That is, in the case where systolic BP values $BP_{SYS}$ of the patient are determined as estimated (monitored) BP values, EBP, the coefficients α, β of the expression (2) or (3) are determined based on the systolic BP value $BP_{SYS}$ determined by the BP determining means 70; in the case where mean BP values $BP_{SYS}$ of the patient are determined as estimated BP values EBP, the coefficients α, β are determined based on the mean BP value $BP_{MEAN}$ determined by the BP determining means 70; and in the case where diastolic BP values $BP_{SYS}$ of the patient are determined as estimated BP values EBP, the coefficients α, β are determined based on the diastolic BP value $BP_{DIA}$ determined by the BP determining means 70.

An estimated-BP-value determining means 78 successively determines, according to the relationship between BP and PWPV-relating information that is represented by the second or third expression (2) or (3), an estimated BP value EBP based on the actual pulse-wave propagation time $DT_{RP}$ or the actual pulse-wave propagation velocity $V_M$ successively obtained by the PWPV-relating-information obtaining means 74.

A pulse-period determining means 82 as another sort of BP-relating-information obtaining means successively determines a pulse period, RR, by measuring a time interval between respective predetermined periodic points on successive heartbeat-synchronous pulses of the ECG waveform detected by the ECG device 34 (e.g., a time interval between the respective R-waves of successive pulses of the ECG waveform).

Figure 4:
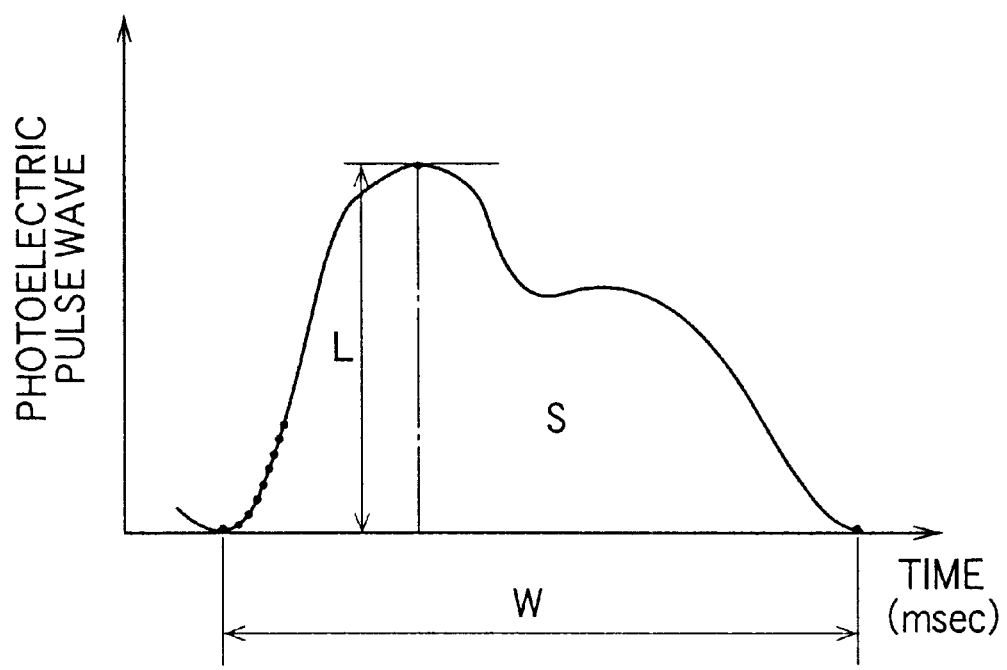
FIG. 4 is a view for explaining a manner in which the control device 28 determines a normalized pulse area, VR.

A pulse-area calculating means 84 as yet another sort of BP-relating-information obtaining means successively calculates a normalized pulse area, VR, by dividing a pulse area, S, defined by each heartbeat-synchronous pulse of the photoelectric pulse wave detected by the probe 38, by the product of a period, W, and an amplitude, L, of that each pulse. However, the pulse-area calculating means 84 may be modified to calculate a normalized pulse area VR for every second, third, . . . , heartbeat-synchronous pulse of the photoelectric pulse wave detected by the probe 38. As illustrated in FIG. 4, the photoelectric pulse wave consists of a series of data points which are input to the control device 28 at a predetermined sampling period of, e.g., several milliseconds or several tens of milliseconds and each of which represents a magnitude of the photoelectric pulse wave. The pulse area S is calculated by integrating (summing) the respective magnitudes of the data points in the pulse period W. Thus, the normalized pulse area VR is calculated according to the expression: VR=S(W×L). The normalized pulse area VR is a dimensionless value indicating the ratio of the pulse area S to the rectangular area defined by the pulse period W and the pulse amplitude L, and is also used with a symbol, % MAP.

A BP-measurement starting means 86 causes the BP determining means 70 and the cuff-pressure control means 72 to start a BP measurement, if the estimated BP value EBP determined by the estimated-BP-value determining means 78 has largely changed from the BP value measured in the last BP measurement and simultaneously if at least one of the pulse period RR and the pulse area VR has largely changed from a corresponding one of the pulse period RR and the pulse area VR measured in the last BP measurement. That is, the BP-measurement starting means 86 includes an EBP-change judging means 87 for judging whether the estimated BP value EBP has largely changed by judging whether the estimated BP value EBP successively determined by the means 78 has changed from the actual BP value measured using the cuff 10 in the last BP measurement, by more than a predetermined value, or more than a predetermined proportion of the last, actual BP value; an RR-change judging means 88 for judging whether the pulse period RR has largely changed by judging whether the pulse period RR successively determined by the pulse-period determining means 82 has changed from the pulse period RR (e.g., the average pulse period RR) measured during the last BP measurement, by more than a predetermined value, or more than a predetermined proportion of the pulse period RR measured during the last BP measurement; and an VR-change judging means 89 for judging whether the pulse area VR has largely changed by judging whether the pulse area VR successively determined by the pulse-area determining means 84 has changed from the pulse area VR (e.g., the average pulse period RR) measured during the last BP measurement, by more than a predetermined value, or more than a predetermined proportion of the pulse area VR measured during the last BP measurement. If the EBP-change judging means 87 judges that the estimated BP value EBP has largely changed and simultaneously if the RR-change judging means 88 judges that the pulse period RR has largely changed or the VR-change judging means 89 judges that the pulse area VR has largely changed, the BP-measurement starting means 86 starts a BP measurement of the cuff-pressure control means 72 and the BP determining means 70. Since the estimated BP value EBP is determined based on the pulse-wave propagation time $DT_{RP}$ or the pulse-wave propagation velocity $V_M$, according to the second or third expression (2) or (3), the EBP-change judging means 87 indirectly judges whether the PWPV-relating information has largely changed.

An abnormality displaying means 90 displays, when the BP-measurement starting means 86 starts a BP measurement of the cuff-pressure control means 72 and the BP determining means 70, at least one character and/or at least one symbol representing the BP-relating information (i.e., the estimated BP value EBP, the pulse period RR, and/or the pulse area VR) whose large change has been judged by the starting means 86 (i.e., the EBP-change judging means 87, the RR-change judging means 88, and/or the VR-change judging means 89), on the display device 32.

A change-proportion determining means 91 determines, after each BP measurement, an amount of change of each estimated BP value EBP successively determined by the EBP determining means 78 after the each BP measurement, from the actual BP value measured in the last BP measurement, and determines a proportion of the amount of change with respect to the actual BP value; determines an amount of change of each pulse period RR successively determined by the RR determining means 82 after the each BP measurement, from the pulse period RR measured in the last BP measurement, and determines a proportion of the amount of change with respect to the latter pulse period RR; and determines an amount of change of each pulse area VR successively determined by the VR determining means 84 after the each BP measurement, from the pulse area VR measured in the last BP measurement, and determines a proportion of the amount of change with respect to the latter pulse area VR.

A BP-relating-information displaying means 92 displays, on the display device 32, respective graphic representations of the actual BP value, the pulse period RR, and the pulse area VR, measured in the last BP measurement, and respective graphic representations of each estimated BP value, each pulse period RR, and each pulse area VR, successively determined by the EBP determining means 78, the RR determining means 82, and the VR determining means 84 after the each BP measurement, so that the patient or a medical staff such as a doctor or a nurse can compare the actual BP value measured in the last BP measurement with the each estimated BP value successively determined by the EBP determining means 78, can compare the pulse period RR measured in the last BP measurement with the each pulse period RR successively determined by the RR determining means 82, and can compare the pulse area VR measured in the last BP measurement with the each pulse area VR successively determined by the VR determining means 84.

Figure 5:
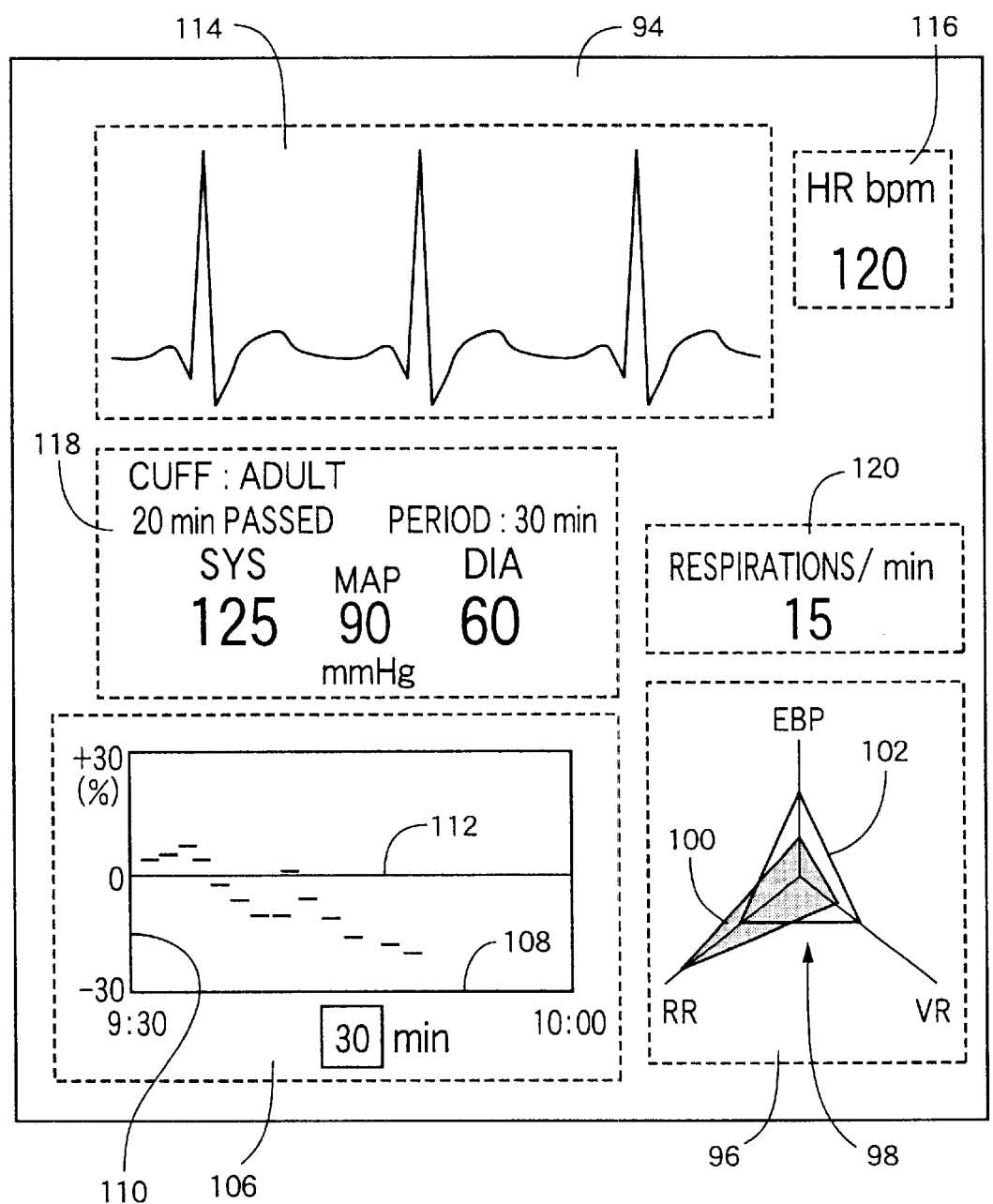
FIG. 5 is a view for explaining reference BP-relating information and actual BP-relating information which are displayed on a display device 32 and are compared with each other by the control device 28 to judge whether a BP measurement using a cuff 10 is to be started.

FIG. 5 shows a display screen 94 of the display device 32 that displays the above-indicated graphic representations. The display screen 94 includes a BP-relating-information display area 96 in which the BP-relating-information displaying means 92 displays a radar chart 98 defined by three axes which intersect one another at the origin and which represent estimated BP value EBP, pulse period RR, and pulse area VR, respectively. The radar chart 98 shows a reference triangle 102 whose apexes represent the actual BP value, the pulse period RR, and the pulse area VR, measured in the last BP measurement, respectively; and a change-proportion triangle 100 whose apexes represent the respective proportions (%) of respective amounts of change of each estimated BP value, each pulse period RR, and each pulse area VR, successively determined by the EBP determining means 78, the RR determining means 82, and the VR determining means 84 after the last BP measurement. The respective proportions (%) of the respective amounts of change of each estimated BP value, each pulse period RR, and each pulse area VR are ones which have been determined by the change-proportion determining means 91. Thus, the patient or the medical staff can compare, on the display screen 94, can compare the actual BP value measured in the last BP measurement with each estimated BP value successively determined by the EBP determining means 78, can compare the pulse period RR measured in the last BP measurement with each pulse period RR successively determined by the RR determining means 82, and can compare the pulse area VR measured in the last BP measurement with each pulse area VR successively determined by the VR determining means 84.

An estimated-BP-value-change displaying means 104 displays, in a maximum-change display area 106 of the display screen 94, a two-dimensional coordinate system having a time axis 108 representing time and a change-proportion axis 110 representing proportion (%) of amount of change of each estimated BP value from the BP value measured in the last BP measurement. The coordinate system shows a time-wise change of the respective proportions of the respective amounts of change of the estimated BP values EBP that are successively determined by the change-proportion determining means 91. The coordinate system includes a reference line 112 which represents the BP value measured in the last BP measurement and which intersects the change-proportion axis 110 at reference point (0%), and extends parallel to the time axis 108. The time axis 108 has a length corresponding to a predetermined BP-measurement period at which BP measurements are periodically carried out by the present BP monitor apparatus 8. Therefore, the patient or the medical staff can compare, on the display screen 94, the BP value measured in the last BP measurement with the most deviated one of the estimated BP values EBP determined by the EBP determining means 78 after the last BP measurement. The absolute value of the difference between the BP value measured in the last BP measurement and the most deviated estimated BP value EBP is not smaller than that of the difference between the BP value measured in the last BP measurement and any other estimated BP value EBP determined after the last BP measurement. Thus, the EBP-change displaying means 104 functions as a maximum-change displaying means. Based on this comparison, the patient or the medical staff can easily determine, and input, a reference value which is to be used by the BP-measurement starting means 86 in judging whether or not to start a BP measurement.

As shown in FIG. 5, the display screen 94 includes, in addition to the BP-relating-information display area 96 and the maximum-change display area 106, an ECG display area 114 in which the ECG waveform is displayed; a heart-rate display area 116 in which a heart rate, HR, (bpm: beats per minute) of the patient is displayed; a BP display area 118 in which the predetermined BP measurement period or interval, the time which has passed after the last BP measurement, and the BP values measured using the cuff 10 in the last BP measurement are displayed; and a respiration-rate display area 120 in which a respiration rate (i.e., respirations per minute) of the patient is displayed.

Hereinafter, there will be described the operation of the control device 28 of the BP monitor apparatus 8 constructed as described above, by reference to the flow charts of FIGS. 6 and 7 that represent the control programs pre-stored in the ROM 31.

Figure 6:
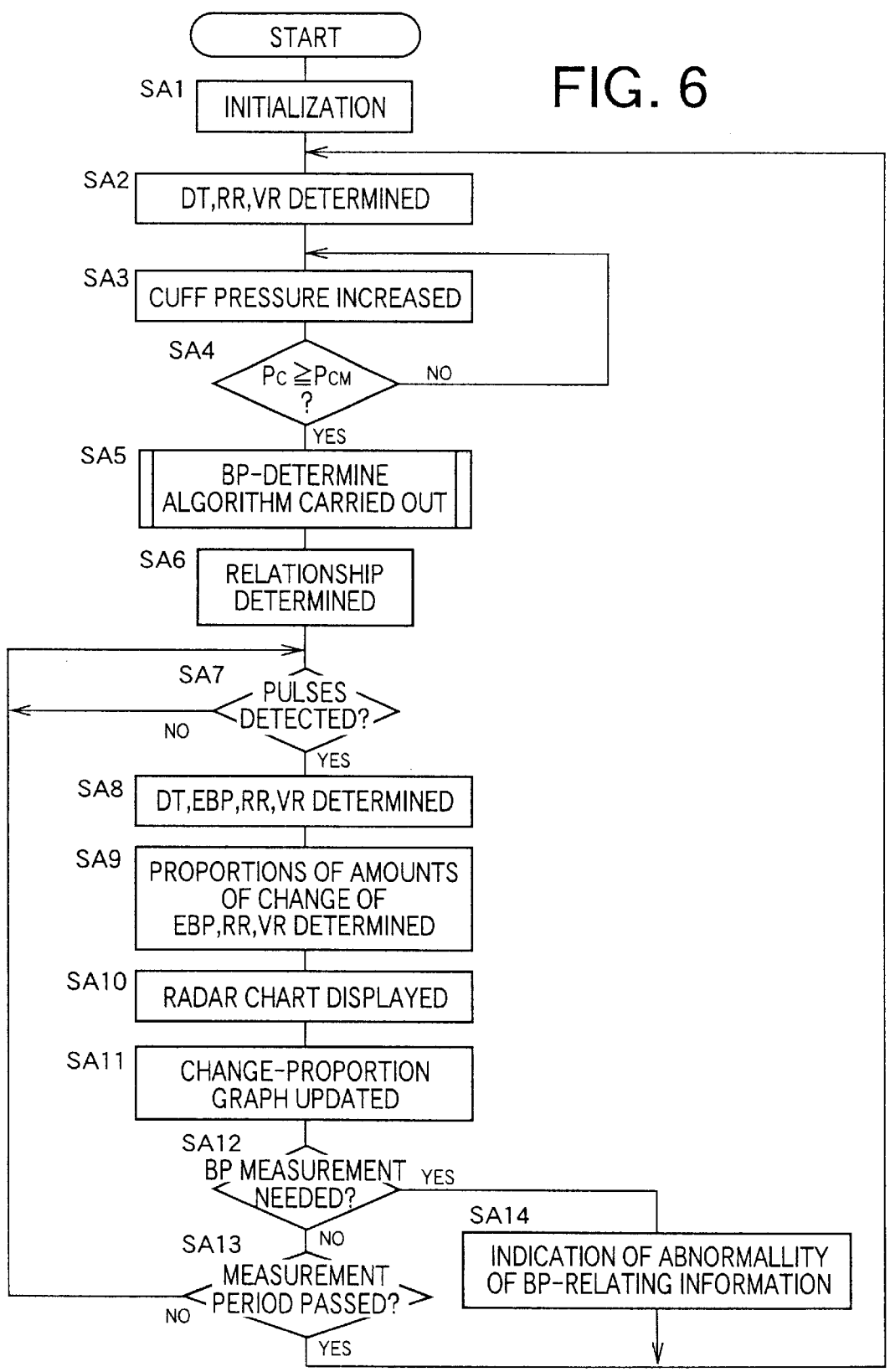
FIG. 6 is a flow chart representing a BP monitor routine which is carried out by the control device 28 to control the BP monitor apparatus.

First, at Step SA1 of FIG. 6, flags, counters, and registers (not shown) of the control device 28 are initialized. Step SA1 is followed by Step SA2 corresponding to the PWPV-relating-information obtaining means 74, the pulse-period determining means 82, and the pulse-area determining means 84. At Step SA2, the control device 28 or the CPU 29 thereof determines, immediately before the cuff pressure is increased by the cuff-pressure control means 72, a propagation time $DT_{RP}$ by measuring a time difference between an R wave of a pulse of the ECG waveform detected by the ECG device 34 and a rising point of a corresponding pulse of the photoelectric pulse wave detected by the probe 38, determines a pulse period RR by measuring a time difference of the R wave of the current pulse of the ECG waveform from that of the preceding pulse of the same, and determines a normalized pulse area VR based on the current pulse of the photoelectric pulse wave.

Step S2 is followed by Steps SA3 and SA4 corresponding to the cuff-pressure control means 72. At Step SA3, the switch valve 16 is switched to the pressure-supply state and the air pump 18 is operated, so that the air pressure in the cuff 10 is quickly increased for a blood-pressure measurement. At Step SA4, it is judged whether the cuff pressure $P_C$ has reached the predetermined target value $P_{CM}$ (e.g., 180 mmHg). If a negative judgment is made at Step SA4, Steps SA3 and SA4 are repeated to continue increasing the cuff pressure $P_C$.

Meanwhile, if a positive judgment is made at Step SA4, Step SA4 is followed by Step SA5 corresponding to the BP determining means 70. At Step SA5, a BP determining algorithm is carried out. More specifically described, the air pump 18 is stopped and the switch valve 16 is switched to the slow-deflation state, so that the cuff pressure PC is slowly decreased at the predetermined low rate (e.g., 3 mmHg/sec). Based on the change of respective amplitudes of successive pulses of the pulse-wave signal $SM_1$ detected during this slow deflation of the cuff 10, the control device 28 determines a systolic BP value $BP_{SYS}$, a mean BP value $BP_{MEAN}$, and a diastolic BP value $BP_{DIA}$ of the patient, according to a well-known oscillometric BP determining algorithm. In addition, the control device 28 determines a pulse rate based on a time difference between two successive pulses of the pulse-wave signal SM1. The control device 28 commands the display device 32 to display the thus measured BP values and pulse rate, and causes the switch valve 16 to be switched to the quick-deflation state so that the cuff pressure $P_C$ is quickly decreased to the atmospheric level.

Step SA5 is followed by Step SA6 corresponding to the relationship determining means 76. At Step SA6, the control device 28 determines a relationship between estimated blood pressure EBP and propagation time $DT_{RP}$. More specifically described, the control device 28 determines a relationship between estimated systolic, mean, or diastolic blood pressure $EBP_{SYS}$, $EBP_{MEAN}$, or $EBP_{DIA}$ and propagation time $DT_{RP}$, i.e., the above-indicated expression (2), based on one of the systolic, mean, or diastolic BP value $BP_{SYS}$, $BP_{MEAN}$, or $BP_{DIA}$ determined at Step SA5 and the propagation time DTRP determined at SA2. This relationship is used to determine, based on the propagation time $DT_{RP}$ determined at Step SA2, an estimated BP value EBP at the time when the last BP measurement using the cuff 10 was carried Out. This estimated BP value EBP is equal to the actual BP value measured in the last BP measurement using the cuff 10.

Step SA6 is followed by Step SA7 to judge whether the control device 28 has received an R wave of a pulse of the ECG waveform and a rising point of a corresponding pulse of the photoelectric pulse wave. If a negative judgment is made at Step SA7, the control device 28 repeats Step SA7. Meanwhile, if a positive judgment is made at Step SA7, Step SA7 is followed by Step SA8 corresponding to the PWPV-relating-information obtaining means 74, the pulse-period determining means 82, the pulse-area determining means 84, and the EBP determining means 78. Like at Step SA2, the control device 28 determines a propagation time $DT_{RP}$ by measuring a time difference between the R wave of the current pulse of the ECG waveform and the rising point of the corresponding pulse of the photoelectric pulse wave, determines a pulse period RR by measuring a time difference of the R wave of the current pulse of the ECG waveform from that of the preceding pulse of the same, and determines a normalized pulse area VR based on the current pulse of the photoelectric pulse wave. In addition, the control device 28 determines an estimated BP value EBP based on the thus determined propagation time $DT_{RP}$ according to the relationship determined at Step S6.

Step SA8 is followed by Step SA9 corresponding to the change-proportion determining means 91. At Step SA9, the control device 28 calculates respective amounts of change of the estimated BP value EBP, the pulse period RR, and the pulse area VR determined at Steps SA8, from the estimated BP value EBP, the pulse period RR, and the pulse area VR determined at Steps SA2 and SA6, respectively, and calculates respective proportions (%) of the thus calculated respective amounts of change of the estimated BP value EBP, the pulse period RR, and the pulse area VR determined at Steps SA8, with respect to the estimated BP value EBP, the pulse period RR, and the pulse area VR determined at Steps SA2 and SA6, respectively.

Step SA9 is followed by Step SA10 corresponding to the BP-relating-information displaying means 92. As indicated in the BP-relating-information display area 96 of the display device 32, shown in FIG. 5, the control device 28 displays, in the radar chart 98, the reference triangle 102 whose apexes represent the estimated BP value EBP, the pulse period RR, and the pulse area VR, at the time when the last BP measurement was carried out, respectively, and the change-proportion triangle 100 whose apexes represent the respective proportions (%) of respective amounts of change of the estimated BP value, the pulse period RR, and the pulse area VR, determined at Step SA9, respectively. When the patient's condition can be considered as being normal, that is, if the respective amounts of change of the estimated BP value, the pulse period RR, and the pulse area VR, determined at Step SA8, have not been deviated so much from the estimated BP value EBP, the pulse period RR, and the pulse area VR, at the time when the last BP measurement was carried out, that is, if the change-proportion triangle 100 has not been deviated so much from the reference triangle 102, the control device 28 commands the display device 32 to display the change-proportion triangle 100 with a color (e.g., green) indicating the normal condition. On the other hand, if the amount of deviation of the change-proportion triangle 100 from the reference triangle 102 is increased and eventually does not fall within a predetermined reference range, the display device 32 displays the change-proportion triangle 100 with a different color, e.g., first yellow and then red.

Step SA10 is followed by Step SA11 corresponding to the EBP-change displaying means 104. At Step SA11, the control device 28 updates, based on the proportion of the amount of change of the estimated BP value EBP that was determined at Step SA9, a graph representing, on the two-dimensional coordinate system in the maximum-change display area 106 of the display screen 94, the time-wise change of respective proportions of respective amounts of change of the estimated BP values EBP that are successively determined by the change-proportion determining means 91. Depending upon the respective deviations of the change proportions (%) as the data points of the graph, from the origin (0%) of the change-proportion axis 110, the data points (indicated at symbols "−" in FIG. 5) are displayed with different colors, so that the patient or the medical staff can easily recognize those deviations. For example, if a change proportion as a data point of the graph falls within the first range of from −10% to +10%, the data point is displayed with green; if a change proportion as a data point falls within the second range of from −20% to −10% or from +10% to +20%, the data point is displayed with yellow; and if a change proportion as a data point does not fall within the first or second range, the data point is displayed with red.

Step SA11 is followed by Step SA12 corresponding to the BP-measurement starting means 86. At Step SA12, the control device 28 carries out the BP-measurement-start judging routine represented by the flow chart of FIG. 7, and if the control device 28 judges that the estimated BP value EBP determined at Step SA8 has largely changed from the EBP value at the time of the last BP measurement and simultaneously if at least one of the pulse period RR and the pulse area VR determined at Step SA8 has largely changed from a corresponding one of the pulse period RR and the pulse area VR measured in the last BP measurement, the control device 28 causes the cuff-pressure control means 72 and the BP determining means 70 to start a BP measurement.

Figure 7:
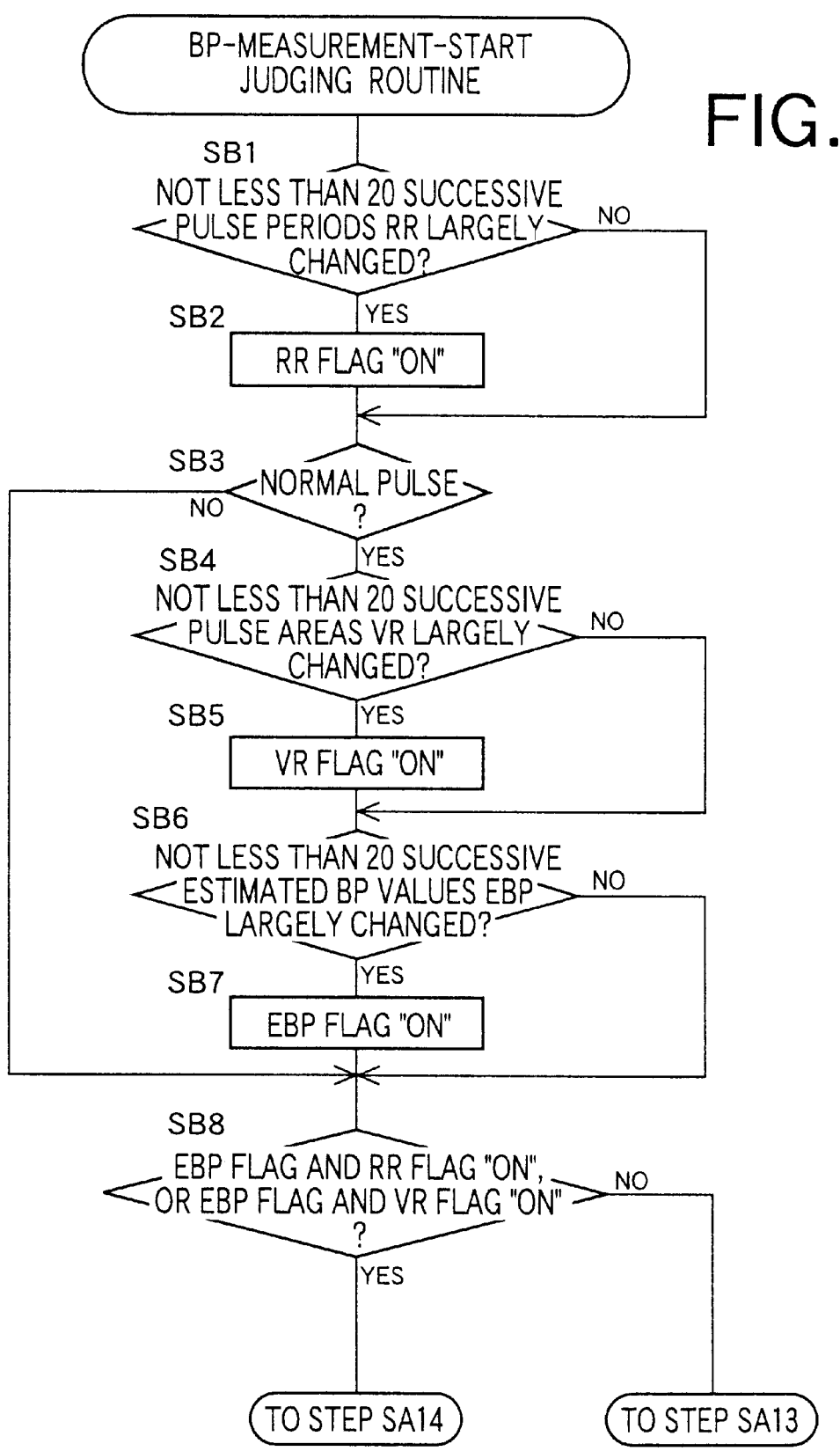
FIG. 7 is a flow chart representing a BP-measurement-start judging routine which is carried out at Step SA12 of FIG. 6 by the control device 28.

First, at Step SB1 of the flow chart of FIG. 7, corresponding to the RR-change judging means 88, the control device 28 judges whether the respective proportions of respective amounts of change of not less than a predetermined number (e.g., 20) of successive pulse periods RR each determined at Step SA9 in not less than the same number of successive control cycles according to the routine of FIG. 7 do not fall within the range of from −5% to +5%. If not, the control device 28 judges that the pulse periods RR have largely or significantly changed. If the pulse periods RR have not largely changed, the control goes to Step SB3 and the following steps. On the other hand, if the pulse periods RR have largely changed, the control goes to Step SB2 to set an RR flag to an "ON" state indicating that the pulse periods RR have largely changed.

Step SB2 is followed by SB3 to judge whether the waveform of the pulse of the photoelectric pulse wave, detected at Step SA7, is normal. This step is provided for removing one or more pulses each having an abnormal waveform, such as a pulse whose waveform has a base line inclined by more than a reference angle, or a pulse whose waveform is discontinued by the calibration of the relationship at Step SA6. If a negative judgment is made at Step SB3, the control goes to Step SB8 and the following steps. On the other hand, if a positive judgment is made, the control goes to Step SB4 corresponding to the VR-change judging means 89.

At Step SB4, the control device 28 judges whether the respective proportions of respective amounts of change of not less than a predetermined number (e.g., 20) of successive normalized pulse areas VR each determined at Step SA9 in not less than the same number of successive control cycles according to the routine of FIG. 7 do not fall within the range of from −3% to −3% If not, the control device 28 judges that the pulse areas VR have largely or significantly changed. If the pulse areas VR have not largely changed, the control goes to Step SB6 and the following steps. On the other hand, if the pulse areas VR have largely changed, the control goes to Step SB5 to set a VR flag to an "ON" state indicating that the pulse areas VR have largely changed.

Step SB5 is followed by Step SB6 corresponding to the EBP-change judging means 87. At Step SB6, the control device 28 judges whether the respective proportions of respective amounts of change of not less than a predetermined number (e.g., 20) of successive estimated BP values EBP each determined at Step SA9 in not less than the same number of successive control cycles according to the routine of FIG. 7 do not fall within the range of from −30% to −30%. If not, the control device 28 judges that the estimated BP values EBP have largely or significantly changed. If the estimated BP values EBP have not largely changed, the control goes to Step SB8 and the following steps. On the other hand, if the estimated BP values EBP have largely changed, the control goes to Step SB7 to set an EBP flag to an "ON" state indicating that the estimated BP values EBP have largely changed.

Step SB7 is followed by Step SB8 to judge whether the EBP flag and the RR flag are both in the "ON" state, or whether the EBP flag and the VR flag are both in the "ON" state. If a negative judgment is made at Step SB8, the control goes to Step SA13 of FIG. 6. At Step SA13, the control device 28 judges whether, after the last BP measurement using the cuff 10 at Step SA5, time has passed by a predetermined measurement (i.e., calibration) period (e.g., 15 or 20 minutes). If a negative judgment is made at Step SA13, the control device 28 carries out Step SA7 and the following steps to repeat the BP monitor routine, i.e., successively determine an estimated BP value EBP, a pulse period RR, and a pulse area VR based on each of successive heartbeat-synchronous pulses of each of the ECG waveform and the photoelectric pulse wave, and display the thus determined values EBP, RR, VR in the radar chart 98 in the BP-relating-formation display area 96 of the display screen 94. From the radar chart 98, the patient or the medical staff can judge, in the case where a negative judgment is made at Step SB8 and accordingly a BP measurement is not started, whether the condition of the patient is actually near abnormality which needs a BP measurement, or near normality which does not need it.

On the other hand, if a positive judgment is made at Step SA13, the control device 28 carries out Step SA2 and the following steps, i.e., the calibration routine, to update the relationship at Step SA6. In addition, if a positive judgment is made at Step SB8, the control goes to Step SA14 of FIG. 6 corresponding to the abnormality displaying means 90. At Step SA14, the control device 28 commands the display device 32 to display characters or symbols representing one or more sorts of BP-relating-information corresponding to one or more of the RR flag, the VR flag, and the EBP flag that is or are in the "ON" state. For example, in the case where the estimated BP values EBP and the pulse periods RR have largely or significantly changed, the display device 32 displays the characters indicating that the estimated BP values EBP and the pulse periods RR have largely changed. Step SA14 is followed by Step SA2 and the following steps to update the relationship at Step SA6. Thus, a BP measurement using the cuff 10 is started. Since the radar chart 96 continues to indicate the estimated BP value EBP, the pulse period RR, and the pulse area VR at the time when the positive judgment is made at Step SA12, the patient or the medical staff can judge which one of the three sorts of BP-relating-formation EBP, RR, VR has largely changed.

As is apparent from the foregoing description, the present BP monitor 8 displays, in the radar chart 98 in the BP-relating-formation display area 96 in the display screen 94, both the reference triangle 102 whose apexes represent the estimated BP value EBP, the pulse period RR, and the pulse area VR at the time of the last BP measurement using the cuff 10, and the change-proportion triangle 100 whose apexes represent the respective proportions of respective amounts of change of the estimated BP value EBP, the pulse period RR, and the pulse area VR that are determined at Step SA9, in each of successive control cycles according to the routine of FIG. 6, after the last BP measurement. Therefore, the patient or the medical staff can recognize to what degree each of the estimated BP value, the pulse period RR, and the pulse area VR, determined at Step SA9 in each of successive control cycles, has changed from a corresponding one of the three values EBP, RR, VR at the time of the last BP measurement.

In addition, the two-dimensional coordinate system in the maximum-change display area 106 of the display screen 94 shows both the reference line 112 which represents the estimated BP value EBP at the time of the last BP measurement using the cuff 10, and the time-wise change of the respective proportions of respective amounts of change of the estimated BP values EBP that are determined at Step SA9, in each of successive control cycles according to the routine of FIG. 6, after the last BP measurement. In addition, the time axis 108 represents the time interval (i.e., the predetermined BP-measurement period) between the last BP measurement and the next BP measurement. Therefore, the patient or the medical staff can recognize, on the display screen 94, to what degree the most deviated one of all the estimated BP values EBP obtained after the last BP measurement has changed from the estimated BP value at the time of the last BP measurement.

While the present invention has been described in its preferred embodiment, it is to be understood that the present invention may otherwise be embodied.

For example, in the illustrated embodiment, the radar chart 98 displayed in the BP-relating-information display area 96 shows the reference triangle 102 whose apexes represent the estimated BP value, the pulse period RR and the pulse area VR at the time of the last BP measurement, and the change-proportion triangle 100 whose apexes represent the estimated BP value, the pulse period RR and the pulse area VR that are determined at Step SA9 in each of successive control cycles according to the routine of FIG. 6 after the last BP measurement. However, the radar chart 98 displayed in the BP-relating-information display area 96 may be replaced with three bar graphs shown in FIG. 8, or a time-wise changing graph shown in FIG. 9.

Figure 8:
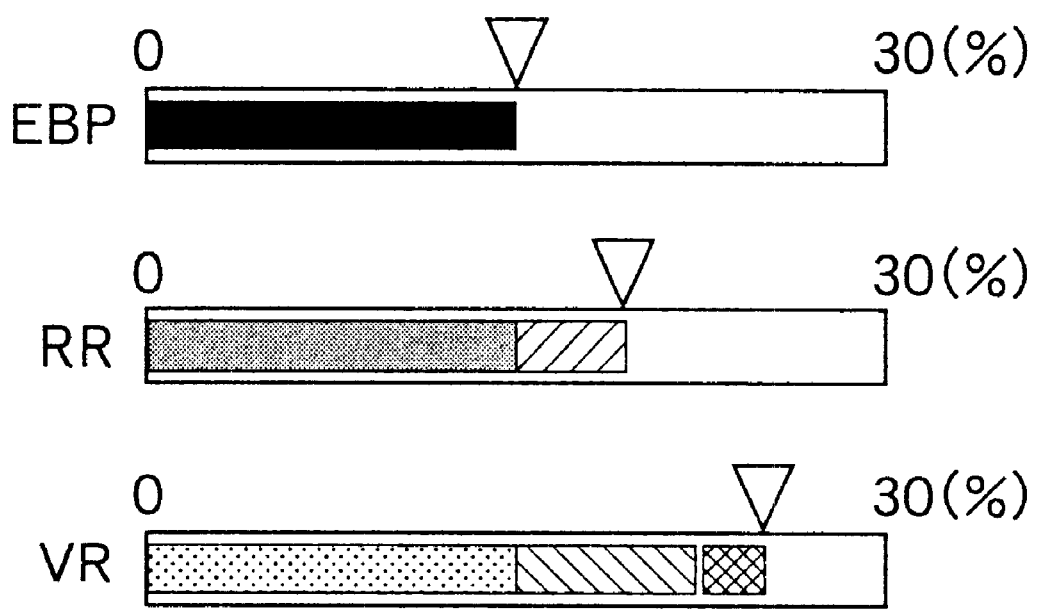
FIG. 8 is a view showing respective proportions of respective amounts of change of an estimated BP value, EBP, a pulse period, RR, and a pulse area, VR, that are displayed, in place of a radar chart 98 (FIG. 5), in a BP-relating-information display area 96 of a display screen 94 of a display device 32 which is employed in another BP monitor apparatus as a second embodiment of the present invention.

In FIG. 8, three inverted triangles "∇" indicate the respective proportions of respective amounts of change of the estimated BP value, the pulse period RR and the pulse area VR that are determined at Step SA9 in each of successive control cycles according to the routine of FIG. 6 after the last BP measurement. Respective origins (0%) of the three bar graphs represent the estimated BP value, the pulse period RR and the pulse area VR at the time of the last BP measurement using the cuff 10. Therefore, the three inverted triangles "∇" correspond to the change-proportion triangle 100 shown in FIG. 5, and the respective origins (0%) of the three bar graphs correspond to the reference triangle 102 shown in FIG. 5. However, in the embodiment shown in FIG. 8, the three inverted triangles "∇" indicate respective absolute values of the respective proportions of respective amounts of change of the estimated BP value, the pulse period RR and the pulse area VR. Depending upon the respective deviations of the absolute values of the change proportions (%) from the corresponding origins (0%), the bar graphs are displayed, in steps, with different colors, so that the patient or the medical staff can easily recognize those steps of the deviations.

Figure 9:
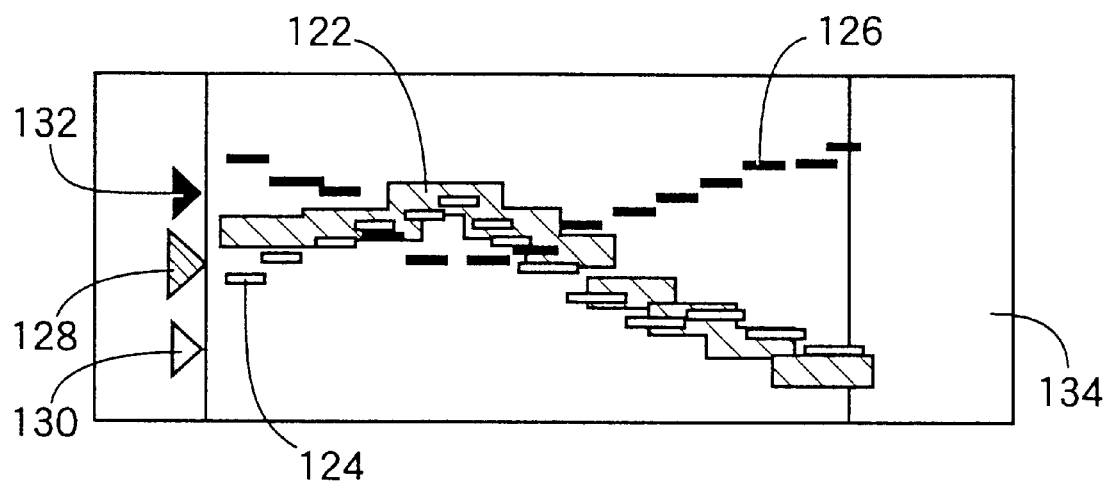
FIG. 9 is a view showing respective proportions of respective amounts of change of an estimated BP value EBP, a pulse period RR, and a pulse area VR that are displayed, in place of the radar chart 98 (FIG. 5), in a BP-relating-information display area 96 of a display screen 94 of a display device 32 which is employed in another BP monitor apparatus as a third embodiment of the present invention.

FIG. 9 shows a graph representing, along a common time axis, a time-wise change 122 of the respective proportions of respective amounts of change of the estimated BP values EBP successively determined after the last BP measurement using the cuff 10; a time-wise chance 124 of the respective proportions of respective amounts of change of the pulse periods RR successively determined after the last BP measurement; and a time-wise change 126 of the respective proportions of respective amounts of change of the pulse areas VR successively determined after the last BP measurement. The graph includes, at the left-hand end thereof, an EBP reference mark 128, an RR reference mark 130, and a VR reference mark 132 which indicate the estimated BP value EBP, the pulse period RR, and the pulse area VR at the time of the last BP measurement, respectively, so as so that the EBP reference mark 128, the RR reference mark 130, and the VR reference mark 13 can be compared with the current estimated BP value EBP, the current pulse period RR, and the current pulse area VR, respectively, which are determined after the last BP measurement. Thus, the three marks 128, 130, 132 correspond to the reference triangle 102 shown in FIG. 5. The graph shown in FIG. 9 includes, at the right-hand end thereof, a blank area 134 which is provided for the patient or the medical staff to be able to recognize that the three sorts of BP-relating information are being successively obtained and estimate, based on the time-wise changes 124, 126, 128, respective future changes of those sorts of BP-relating information. In addition, one of the three sorts of BP-relating information (e.g., the estimated BP values EBP) is selected, in advance, as being the most important for the monitoring of the blood pressure of the patient, and the time-wise change of the most important sort of information (e.g., the time-wise change 122) is displayed in thicker lines or symbols than the respective time-wise changes of the other sorts of information (e.g., the time-wise changes 124, 126), as shown in FIG. 9, so that the most important sort of information can be more easily observed than the other sorts of information.

Figure 10:
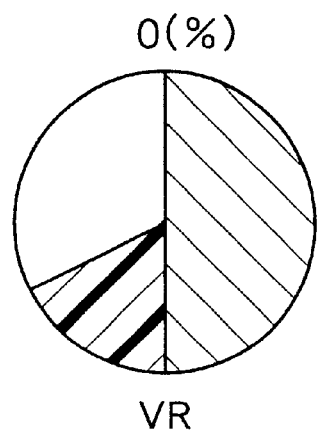
FIG. 10 is a view showing a proportion of an amount of change of a pulse area VR that is displayed, in place of the radar chart 98 (FIG. 5), in a BP-relating-information display area 96 of a display screen 94 of a display device 32 which is employed in another BP monitor apparatus as a fourth embodiment of the present invention.

In the illustrated embodiment, the three sorts of BP-relating information, that is, the estimated BP value, the pulse period RR, and the pulse area VR are employed. However, since each of the three sorts of BP-relating information reflects the change of blood pressure of a living subject, it is possible to use only one or two of the three sorts of information. Each of FIG. 10 and FIG. 11 shows a graph which represents a single sort of BP-relating information and which may be displayed in place of the radar chart 98

(FIG. 5) in the BP-relating-information display area 96. FIG. 10 shows a circle graph corresponding to the bar graph shown in FIG. 8, and representing the proportion (%) of amount of change (absolute value) of each of the pulse areas VR successively determined after the last BP measurement. The origin (0%) of the circle graph represents the pulse area VR at the time of the last BP measurement and corresponds to the reference triangle 102 shown in FIG. 5. Like the bar graph shown in FIG. 8, the circle graph is displayed, in steps, with different colors, depending upon the respective amounts of deviation of the successively determined pulse areas VR from the pulse area VR at the time of the last BP measurement. FIG. 11 shows an arrow 136 which represents the proportion (%) of amount of change (absolute value) of each of the estimated BP values EBP successively determined after the last BP measurement. The origin (0%) of the circle represents the estimated BP value EBP at the time of the last BP measurement and corresponds to the reference triangle 102 shown in FIG. 5. A background 138 of the arrow 136 is displayed with a first color, when each of the successively determined estimated BP values EBP is smaller than the estimated BP value EBP at the time of the last BP measurement (that is, when the amount of change of the each value EBP is negative); and the background 138 is displayed with a second color different from the first color, when the each of the successively determined estimated BP values EBP is greater than the estimated BP value EBP at the time of the last BP measurement (that is, when the amount of change of the each value EBP is positive). Thus, a person can more easily recognize the change of the estimated BP values EBP.

Figure 12A:
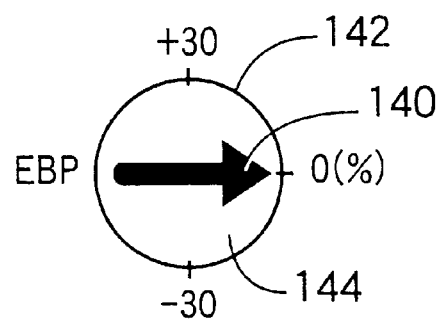
FIGS. 12A, 12B, and 12C are views showing respective proportions of respective amounts of change of estimated BP values EBP each of which is displayed, in place of the radar chart 98 (FIG. 5), in a BP-relating-information display area 96 of a display screen 94 of a display device 32 which is employed in another BP monitor apparatus as a sixth embodiment of the present invention.
Figure 12B:
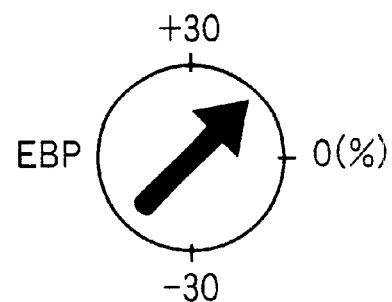
Figure 12C:
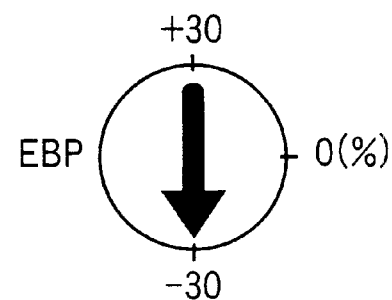

Like FIGS. 10 and 11, FIGS. 12A, 12B, and 12C shows a graph which represents a single sort of BP-relating information and which may be displayed in place of the radar chart 98 (FIG. 5) in the BP-relating-information display area 96. The graph includes an arrow 140 which represents the proportion (%) of amount of change of each of the estimated BP values EBP successively determined after the last BP measurement. The graph shown in FIGS. 12A to 12C differs from the graph shown in FIG. 11, in that the origin (0%) of the former graph that represents the estimated BP value EBP at the time of the last BP measurement and corresponds to the reference triangle 102 shown in FIG. 5, is set at the right-hand one of two points where a horizontal line passing through the center of a circle 142 intersects the circle 142 and in that the former graph can indicate both a positive and a negative proportion (%) corresponding to both a positive and a negative amount of change of each estimated BP value EBP. FIG. 12A shows the arrow 140 indicating a horizontal and rightward direction and thereby indicating that the current estimated BP value EBP has not deviated from the estimated BP value EBP at the time of the last BP measurement; FIG. 12B shows the arrow 140 indicating that the current estimated BP value EBP has increased slightly (e.g. increased by 10%) from the estimated BP value EBP at the time of the last BP measurement; and FIG. 12C shows the arrow 140 indicating that the current estimated BP value EBP has decreased largely (e.g. decreased by 30%) from the estimated BP value EBP at the time of the last BP measurement. In the graph shown in FIGS. 12A to 12C, too, the arrow 140 or a background 144 thereof is displayed, in steps, with respective different colors, depending upon the respective amounts of deviation of the successively determined estimated BP values EBP from the estimated BP value EBP at the time of the last BP measurement. In FIGS. 12A to 12C, the indication of values, 0 (%), +30, and −30, may be eliminated because the inclination of the arrow 140 indicates the proportion of amount of change of each of the successively determined estimated BP values EBP, so that the inclination of the arrow 140 can be compared with the horizontal line indicating the estimated BP value EBP at the time of the last BP measurement.

Figure 13:
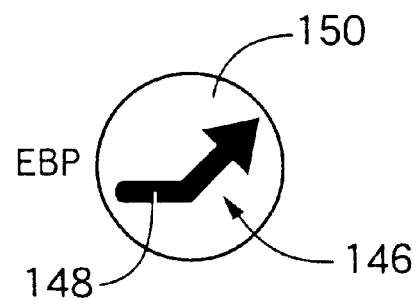
FIG. 13 is a view showing a proportion of an amount of change of an estimated BP values EBP that is displayed, in place of the radar chart 98 (FIG. 5), in a BP-relating-information display area 96 of a display screen 94 of a display device 32 which is employed in another BP monitor apparatus as a seventh embodiment of the present invention.

FIG. 13 also shows a graph which represents a single sort of BP-relating information and which may be displayed in place of the radar chart 98 (FIG. 5) in the BP-relating-information display area 96. The graph includes an arrow 146 which represents the proportion (%) of amount of change of each of the estimated BP values EBP successively determined after the last BP measurement. Like the graph shown in FIGS. 12A to 12C, a head portion of the arrow 146 included in the graph shown in FIG. 13 can indicate both a positive and a negative proportion (%) corresponding to both a positive and a negative amount of change of each estimated BP value EBP. More specifically described, the arrow 146 whose head portion points a horizontal and rightward direction, indicates that the current estimated BP value EBP has not deviated from the estimated BP value EBP at the time of the last BP measurement; the arrow 146 whose head portion is inclined upward, indicates that the current estimated BP value EBP has increased from the estimated BP value EBP at the time of the last BP measurement; and the arrow 146 whose head portion is inclined downward, as shown in FIG. 13, indicates that the current estimated BP value EBP has decreased from the estimated BP value EBP at the time of the last BP measurement. In addition, a base portion 148 from which the head portion 146 extends indicates how the estimated BP value EBP at the time of the last BP measurement has deviated or changed from the estimated BP value EBP at the time of the second last BP measurement, i.e., the measurement preceding the last measurement. Since the base portion 148 shown in FIG. 13 is horizontal, it indicates that the value EBP at the time of the last measurement has not changed from the value EBP at the time of the second last measurement. In the graph shown in FIG. 13, too, the arrow 146 or a background 150 thereof is displayed, in steps, with respective different colors, depending upon the respective amounts of deviation of the successively determined values EBP from the value EBP at the time of the last measurement.

Figure 14:
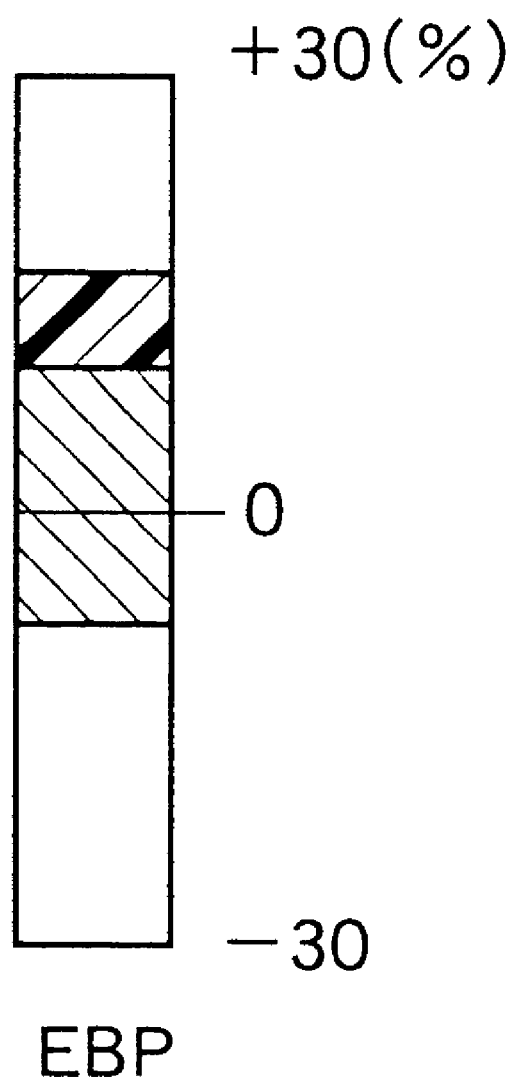
FIG. 14 is a view showing the greatest one of respective proportions of respective amounts of change of estimated BP values EBP that is displayed, in place of a two-dimensional coordinate system defined by two axes 108, 110 (FIG. 5), in a maximum-change display area 106 of a display screen 94 of a display device 32 which is employed in another BP monitor apparatus as an eighth embodiment of the present invention.

In the illustrated embodiment, the maximum-change display area 106 of the display screen 94 shows a time-wise change of the respective proportions (%) of respective amounts of change of the estimated BP values EBP successively determined after the last BP measurement using the cuff 10 and before the next BP measurement. Thus, the patient or the medical staff can recognize, on the display area 106, one of the successively determined values EBP that is most deviated from the value EBP at the time of the last measurement. However, it is possible to display the most deviated one estimated BP value EBP only. In this case, when a value EBP newly determined is more deviated than the current most deviated one value EBP, the newly determined value EBP is adopted as the new most deviated value EBP to replace the current most deviated value EBP being displayed and thereby update the same. An example of this case is shown in FIG. 14, which shows a bar graph representing the proportion (%) of amount of change of the most deviated one estimated BP value EBP obtained after the last BP measurement using the cuff 10, A line indicating the origin (0%) of the bar graph represents the value EBP at the time of the last BP measurement. Likewise, the bar graph shown in FIG. 14 is displayed, in steps, with respective different colors, depending upon the respective amounts of deviation of the successively determined values EBP from the value EBP at the time of the last measurement.

In the illustrated embodiment, the maximum-change display area 106 of the display screen 94 shows the most deviated one of the estimated BP values EBP as a sort of BP-relating information. However, it is possible to display, in the display area 106, the most deviated value of a different sort of BP-relating information, such as pulse-rate-relating information (e.g., pulse period RR, pulse rate HR, etc.) or pulse area VR. Otherwise, it is possible to display, in the area 106, the respective most deviated values of plural sorts of BP-relating information. In the last case, the patient or the medical staff can visually compare the respective most deviated values of plural sorts of BP-relating information, with the respective values of those sorts of information at the time of the last measurement. Therefore, the person can easily judge whether each of the respective threshold values used, for those sorts of information, in judging whether a BP measurement should be started, is appropriate or not.

In the illustrated embodiment, the radar chart 98 shown in the BP-relating-information display area 96 includes the reference triangle 102 representing the respective values of the plural sorts of BP-relating information (i.e., the estimated BP value EBP, the pulse period RR, and the pulse area VR) at the time of the last BP measurement, and the change-proportion triangle 100 representing the respective proportions of respective amounts of change of the respective current values of those sorts of information, successively determined by the change-proportion determining means 91, so that the reference triangle 102 and the change-proportion triangle 100 can be compared with each other. However, it is possible to display a graph including the respective values of the plural sorts of BP-relating information at the time of the last BP measurement, and the respective current values of those sorts of information, successively determined by the change-proportion determining means 91, after the last BP measurement. Likewise, it is possible to display, in the maximum-change display area 106, a graph including the value or values of one or more sorts of BP-relating information at the time of the last BP measurement, and the most deviated value or values of that or those sorts of information determined after the last measurement.

In the illustrated embodiment, the estimated BP value is employed as a sort of BP-relating information. However, since the value EBP corresponds, one by one, to the pulse-wave propagation time $DT_{RP}$ or the pulse-wave propagation velocity $V_M$, as indicated by the mathematical expressions (2), (3), the propagation time $DT_{RP}$ or the propagation velocity $V_M$ may be used in place of the value or information EBP.

In the illustrated embodiment, the pulse period RR is employed as a sort of BP-relating information. However, since the pulse period RR (sec) corresponds, one by one, to the pulse rate HR (beats/min) according to the following expression: HR=60/RR, the heart rate HR may be employed, in place of the pulse period RR, by the RR determining means 82, the RR-change judging means 88, the change-proportion determining means 91, and the BP-relating-information displaying means 92.

The BP monitor apparatus 8 shown in FIG. 1 utilizes the probe 38 as part of the pulse oximeter, and measures a blood oxygen saturation, SpO2, as a sort of physical information other than the BP-relating information. This physical information may be included in the radar chart 98 shown in FIG. 5, or in the graph shown in FIG. 8 or in each of FIGS. 10 to 14. If the current piece of physical information does not fall within a predetermined reference range, the abnormality displaying means 90 (Step SA14) may command the display device 32 to display characters and/or symbols indicating that the physical information has become abnormal.

In the illustrated embodiment, the abnormality displaying means 90 commands the display device 32 to display characters and/or symbols indicating which one of the above-indicated three sorts of BP-relating information has largely deviated. However, it is possible to employ a speaker (not shown) which produces sound or voice for the same purpose. For example, in the case where the BP monitor apparatus 8 judges that the estimated BP value EBP and the pulse period RR have largely deviated, the speaker outputs a message that respective large deviations of estimated BP value and pulse rate have been detected.

While the present invention has been described in its preferred embodiments, the present invention is not limited to the features described in SUMMARY OF INVENTION and the features described in PREFERRED EMBODIMENTS OF INVENTION and may be embodied with other changes, improvements, and modifications that may occur to a person skilled in the art without departing from the scope and spirit of the invention defined in the appended claims.

What is claimed is:

1. A blood-pressure monitor apparatus, comprising:
   a blood-pressure measuring device which includes an inflatable cuff adapted to apply a pressing pressure to a portion of a living subject and which measures a blood pressure of the subject by changing the pressure of the cuff applied to said portion of the subject;
   a blood-pressure-relating-information obtaining device which iteratively obtains, from the living subject, blood-pressure-relating information which changes with change of the blood pressure of the subject;
   a blood-pressure-measurement starting means for starting a blood-pressure measurement of the blood-pressure measuring device, when a subsequent piece of blood-pressure-relating information obtained by the blood-pressure-relating-information obtaining device after the blood-pressure measuring device has measured a last blood pressure of the living subject in a last blood pressure measurement thereof has deviated by not less than a predetermined amount from an initial piece of blood-pressure-relating information obtained by the obtaining device when the blood-pressure measuring device measured the last blood pressure of the subject;
   a display device which displays a graph representing the pieces of blood-pressure-relating information obtained by the blood-pressure-relating-information obtaining device; and
   a control device which comprises a determining means for determining a proportion of an amount of change, from said initial piece of blood-pressure-relating information, of each one of subsequent pieces of blood-pressure-relating information iteratively obtained by the obtaining device after the blood-pressure measuring device has measured the last blood pressure of the subject; and a control means for controlling the display device to display the graph representing the initial piece of blood-pressure-relating information and the determined proportion of the amount of change of said each one of subsequent pieces of blood-pressure-relating information, so that the initial piece of blood-pressure-relating information and the determined proportion of the amount of change of said each one subsequent piece of blood-pressure-relating information can be compared with each other on the display device.

2. An apparatus according to claim 1, wherein the blood-pressure-relating information obtaining device comprises a first obtaining means for iteratively obtaining, from the living subject, a first sort of blood-pressure-relating information which changes with change of the blood pressure of the subject; a second obtaining means for iteratively obtaining, from the living subject, a second sort of blood-pressure-relating information which changes with change of the blood pressure of the subject; and a third obtaining means for iteratively obtaining, from the living subject, a third sort of blood-pressure-relating information which changes with change of the blood pressure of the subject.

3. An apparatus according to claim 2, wherein the determining means determines a proportion of an amount of change of each one of subsequent pieces of each of the first, second, and third sorts of blood-pressure-relating information iteratively obtained by the first, second, and third obtaining means after the blood-pressure measuring device has measured the last blood pressure of the subject, from an initial piece of a corresponding one of the first, second, and third sorts of blood-pressure-relating information obtained by the first, second, and third obtaining means when the blood-pressure measuring device has measured the last blood pressure, and the control means controls the display device to display the graph representing the respective initial pieces of the first, second, and third sorts of blood-pressure-relating information and the respective determined proportions of respective amounts of change of the respective subsequent pieces of the first, second, and third sorts of blood-pressure-relating information, so that each of the respective initial pieces of the first, second, and third sorts of blood-pressure-relating information and a corresponding one of the respective determined proportions of respective amounts of change of the respective subsequent pieces of the first, second, and third blood-pressure-relating information can be compared with each other on the display device.

4. An apparatus according to claim 3, wherein the display device comprises means for displaying the graph in a radar chart which is defined by three axes which intersect one another at a common origin and which represent respective proportions of respective amounts of change of respective subsequent pieces of the first, second, and third sorts of blood-pressure-relating information, the graph comprising a reference triangle having three apexes representing the respective initial pieces of the first, second, and third sorts of blood-pressure-relating information; and a change-proportion triangle having three apexes representing the respective determined proportions of respective amounts of change of the respective subsequent pieces of the first, second, and third sorts of blood-pressure-relating information.

5. An apparatus according to claim 1, wherein the blood-pressure-relating information obtaining device comprises means for obtaining, as the blood-pressure-relating information, at least one of a pulse period and a pulse area from the subject.

6. A blood-pressure monitor apparatus, comprising:
   a blood-pressure measuring device which includes an inflatable cuff adapted to apply a pressing pressure to a portion of a living subject and which measures a blood pressure of the subject by changing the pressure of the cuff applied to said portion of the subject;
   a blood-pressure-relating-information obtaining device which iteratively obtains, from the living subject, blood-pressure-relating information which changes with change of the blood pressure of the subject;
   a blood-pressure-measurement starting means for starting a blood-pressure measurement of the blood-pressure measuring device, when a subsequent piece of blood-pressure-relating information obtained by the blood-pressure-relating-information obtaining device after the blood-pressure measuring device has measured a last blood pressure of the living subject in a last blood pressure measurement thereof has deviated by not less than a predetermined amount from an initial piece of blood-pressure-relating information obtained by the obtaining device when the blood-pressure measuring device measured the last blood pressure of the subject;
   a display device which displays a graph representing the pieces of blood-pressure-relating information obtained by the blood-pressure-relating-information obtaining device; and
   a control device which comprises a determining means for determining a proportion of an amount of change, from said initial piece of blood-pressure-relating information of a most deviated one of subsequent pieces of blood-pressure-relating information iteratively obtained by the obtaining device after the blood-pressure measuring device has measured the last blood pressure of the subject; and a control means for controlling the display device to display the graph representing the initial piece of blood-pressure-relating information and the determined proportion of the amount of change of said most deviated one of subsequent pieces of blood-pressure-relating information, so that the initial piece of blood-pressure-relating information and the determined proportion of amount of the change of said most deviated subsequent piece of blood-pressure-relating information can be compared with each other on the display device, said most deviated subsequent piece of blood-pressure-relating information being more deviated from the initial piece of blood-pressure-relating information, than any other subsequent piece of blood-pressure-relating information.

7. An apparatus according to claim 6, wherein the determining means determines a proportion of an amount of change, from said initial piece of blood-pressure-relating information, of each one of subsequent pieces of blood-pressure-relating information iteratively obtained by the obtaining device after the blood-pressure measuring device has measured the last blood pressure of the subject, and wherein the display device comprises a display means for displaying, in a two-dimensional coordinate system which is defined by a first axis representing time and a second axis representing proportion of amount of change of each one of subsequent pieces of blood-pressure-relating information, the graph comprising a symbol representing the determined proportion of the amount of change of said each one of subsequent piece of blood-pressure-relating information.

8. An apparatus according to claim 7, wherein the display means displays, in the two-dimensional coordinate system, the graph comprising a reference line which represents the last blood pressure of the subject and which extends parallel to the first axis and intersects the second axis at a reference point, 0%, representing the initial piece of blood-pressure-relating information.

9. An apparatus according to claim 7, wherein the blood-pressure measuring device comprises means for measuring a blood pressure of the subject at a predetermined blood-pressure-measurement period, and wherein the display means displays the graph in the two-dimensional coordinate system having the first axis having a length corresponding to the predetermined blood-pressure-measurement period.

10. An apparatus according to claim 7, wherein the display means displays the graph in the two-dimensional coordinate system having the second axis having a length corresponding to said predetermined amount, so that the blood-pressure-measurement starting means starts a blood-pressure measurement of the blood-pressure measuring device, when the determined proportion of the amount of change of one of the subsequent pieces of blood-pressure-relating information is deviated by not less than the predetermined amount from the initial piece of blood-pressure-relating information and does not fall in the two-dimensional coordinate system.

* * * * *